(12) United States Patent
Belmont et al.

(10) Patent No.: US 7,071,339 B2
(45) Date of Patent: Jul. 4, 2006

(54) PROCESS FOR PREPARING FUNCTIONALIZED γ-BUTYROLACTONES FROM MUCOHALIC ACID

(75) Inventors: Daniel Belmont, Howell, MI (US); Ji Zhang, Ann Arbor, MI (US)

(73) Assignee: Warner Lambert Company LLC, Morris Plains, NJ (US)

( * ) Notice: Subject to any disclaimer, the term of this patent is extended or adjusted under 35 U.S.C. 154(b) by 77 days.

(21) Appl. No.: 10/463,612

(22) Filed: Jun. 18, 2003

(65) Prior Publication Data

US 2004/0049058 A1 Mar. 11, 2004

Related U.S. Application Data

(60) Provisional application No. 60/407,019, filed on Aug. 29, 2002, provisional application No. 60/449,181, filed on Feb. 21, 2003.

(51) Int. Cl.
*C07D 307/32* (2006.01)
(52) U.S. Cl. .................................. 549/323; 549/324
(58) Field of Classification Search ................ 549/323, 549/324
See application file for complete search history.

(56) References Cited

U.S. PATENT DOCUMENTS 6,306,910 B1 10/2001 Magnus et al.

FOREIGN PATENT DOCUMENTS

WO WO93/23383 11/1993
WO WO00/76958 12/2000

OTHER PUBLICATIONS

Zhang, J et al 'Metal-mediated allylation o fmucohalic acids: facil formation of gamma-allylic alpha,beta-unsaturated gamma butyrolactones' Tetrahedron Letters 44 (2003) 5579-5582.*
Masuzawa, Y., Synthesis of Both Enantiomers of cis-3-Methyl-4-Decanolide, A Key Component fo the Scent of African Orchids, Nat. Prod. Lett., vol. 13(4), p. 239-246 (1999).
Naoshima, Y., et al., Synthesis of Racemates and (+)-Enantiomers of y-Caprolactone, y-Dodecanolactone and s-Hexadecanolactone, Lactonic Sex Phermones of the Dermestid Bettle, Rove Bettle, and Oriental Hornet, Agric. Biol. Chem., vol. 47(7), p. 1431 (1983).
Hu, G-W., Hecheng Huaxue, vol. 9, p. 167 (2001).
Dufosse, et al., Microbial Production of Flavors for the Food Industry. A Case Study on the Production of Gamma-decalactone, the Key Compound of Peach Flavor, by the Yeasts Sporidiobolus sp., Food Sci. Biotech, vol. 11(2), p. 192-202 (2002).

Li, C-J and Chan, T-H, Organic Syntheses Using Indium-Mediated and Catalyzed Reactions in Aqueous Media, Tetrahedron, vol. 55, p. 11149-11176 (1999).
Gordon, C.M., Indium and tin-mediated allylation in ionic liquids, Green Chemistry, vol. 4, p. 124-128 (2002).
Wang, Z, et al., Application of Tin and Nanometer Tin in Allylation of Carbonyl Compounds in Tap Water, Org. Lett., vol. 4, p. 1683 (2002).
Neumann, W., Tri-n-butyltin Hydride as Reagent in Organic Synthesis, Synthesis, p. 665-683 (1987).
Takashi, Ooi, et al., Practical Oppenauer (OPP) Oxidation of Alcohols with a Modified Aluminum Catalyst, Org. Lett. 4(16), p. 2669-2672 (2002).
Ahmend F. Abel-Magid, et al., Reductive Amination of Aldehydes and Ketones with Sodium Triacetoxyborohydride. Studies on Direct and Indirect Reductive Amination Procedures, J. Org. Chem., 61, p. 3849-3862 (1996).
Kitamura, M., et al., Catalytic Leuchart—Wallach-Type Reductive Amination of Ketones, J. Org. Chem., vol. 67, p. 8685-8687 (2002).
Kobayashi, Catalytic Enatioslectice Addition to Imines, S., Chem. Rev., vol. 99, p. 1069-1094 (1999).

(Continued)

*Primary Examiner*—Amelia A. Owens
(74) *Attorney, Agent, or Firm*—Heidi M. Berven; Suzanne M. Harvey; Charles W. Ashbrook

(57) ABSTRACT

A process for preparing functionalized γ-butyrolactones 3 and various biologically active compounds using mucohalic acid 1 and halide 2 in the presence of indium is disclosed, wherein X, Y, $R_1$, $R_2$, and $R_3$ may have any of the meanings defined herein

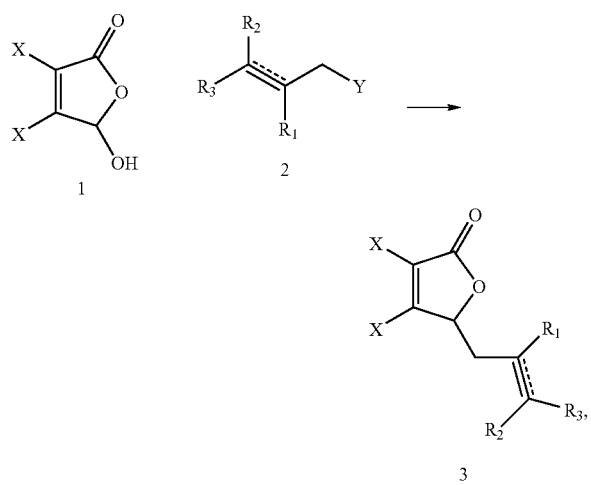

30 Claims, No Drawings

OTHER PUBLICATIONS

Bohm, et al., Enatioselectice Synthesis of (−)-Roccellaric Acid, Org. Letts, vol. 3(9), p. 1315-1318.

Thadani, et al., A Mild Protocol for Allylation and Highly Diasteroselective Syn or Anti Crotylation of Aldehydes in Biphasic and Aqueous Media Utilizing Potassium Allyl- and Crotyltrifluoroborates, Org. Letts, vol. 4(22), p. 3827-3830 (2002).

Nokami, J., New Route to a-Adducts of Homoallylic Alcohols by an Acid-Catalyzed Sterospecific Allyl-Transfer Reaction from y-Adducts, Chem. Eur. J., vol. 6, p. 2902 (2000).

Fernandez, R., et al., Antifungal Metabolites from the Marine Sponge *Pachastrissa* sp.: New Bengamide and Bengazole Derivatives, J. Nat. Prod., vol. 62, p. 678 (1999).

Rodriguez, et al., New Metabolites from the West Indian Sea Feather *Pseudopterogorgia bipinnata*, J. Nat. Prod., vol. 63, p. 1548-1550 (2000).

El Sayad, et al., The Biocatalytic Transformation of Furan to Amide in the Bioactive Marine Natual Product Palinurin, J. Org Chem. vol. 64, p. 9258 (1999).

Liu, Y., et al., New Cytotoxic Sesterterpenes from trhe Sponge *Sarcotragus* Species, J. Nat. Prod., vol. 64, p. 1301-1304 (2001).

Moghaddam, F., et al., Structure and Absolute Sterochemistry of Salvimirzacolide, a New Sesterterpene from *Salvia mirzayanii*, J. Nat Prod., vol. 61, p. 279 (1998).

Liras, S., et al., An Approach to the Skeleton of the Securingega Alkaloids. The Total Synthesis of (±)-Securinine, Org. Letts., vol. 3(5), p. 703-706 (2001).

Schmitz, W., et al., A *b*-Lactone-Based Strategy Applied to the Total Synthesis of (8S,21S,22S,23R)-and (8R,21S,22S,23R)-Okinonellin B, J. Org. Chem., vol. 63, p. 2058-2059 (1998).

Banwell, M., et al., Chemoenzymatic Synthesis of (+)-Aspicilin from Chlorobenzene, Org. Letts., vol. 2(23), p. 3583-3586 (2000).

Han, X., et al., A Short Catalytic Enantioselective Synthesis of the Proinflammatory Eicosanoid 12(R)-Hydroxy-5(Z),8(Z),10(E),14(Z)-eicosatetraenoic Acid (12(R)-HETE), Org. Letts., vol. 2(16), p. 2543-2544 (2000).

Li, C-J., et al., Organometallic Reactions In Aqueous Media with Indium, Tetra. Lett., vol. 32, p. 7017-7020 (1991).

Bernardelli, P., et al., Stereoselective Indium-Promotoed Allylation of y-Hydroxy-y-Lactones under Aqueous Conditions. The Neighboring Carboxyl Effect, J. Org. Chem., vol. 62, p. 8284-8285 (1997).

Choudhury, P., Direct Indium-Promoted Preparation of a-Methylene-y-lactones from 2-(Bromomethyl)acrylic Acid and Carbonyl Compounds, Tetrahedron, vol. 55, p. 10779 (1999).

Choudhury, P., et al., Indium-promoted Preparation of Substituted a-Methylene-y-lactones from 2-(Bromomethyl)acrylic Acid and Carbonyl Compounds, Tetrahedron Lett., vol. 39, p. 3581 (1998).

Nokami, J., et al., Allylation of Aldehydes and Ketones in the Presence of Water by Allylic Bromides, Metallic Tin, and Aluminum, Organometallics, vol. 2, p. 191 (1983).

Yanagisawa A., Highly Chemoselective Allylation of Carbonyl Compounds with Tetraallyltin in Acidic Aqueous Media, J. Am. Chem. Soc., vol. 115, p. 10356 (1993).

Einhorn C., Selective allylation of carbonyl compounds in aqueous media, J. Organomet. Chem., vol. 322, p. 177 (1987) ABSTRACT.

Chan, T., et al., Organometallic Reactions in Aqueous Media. The Nature of the Organotin Intermediate in the Tin-Mediated Allylation of Carbonyl Compounds, J. Org. Chem., vol. 64, p. 4452 (1999).

Wang, Z., et al., Application of Tin and Nanometer Tin in Allylation of Carbonyl Compounds in Tap Water, Org. Lett., vol. 4, p. 1683 (2002).

Trost, B., Ruthenium-Catalyzed Cycloisomerization-Oxidation of Homopropargyl Alcohols. A New Access to y-Butyrolactones, J. Am. Chem. Soc., vol. 121, p. 11680 (1999).

Wu, Y., et al., Synthesis of Natural Fragrant Molecules cis-3-Methyl-4-decanolide and Aeerangis Lactone. General Enantioselective Routes to B,y-cis-Disubstituted y-Lactones and y,s-cis-Disubstituted s-Lactones, J. Org. Chem., vol. 67, p. 3802 (2002).

Mino, T., et al., Syntesis of Lactones by Baeyer-Villiger Oxidation with Magnesium Monoperphthate Hexahydrate, J. Org. Chem., vol. 62, p. 2633 (1997).

Masuzawa, Y., Synthesis of Both Enantiomers of cis-3-Methyl-4-Decanolide, A Key Component for the Scent of African Orchids, Nat. Prod. Lett., vol. 13, p. 239 (1999).

Fernandez, A-M., et al., Optical;ly Pure Dihydroxy y-Alkylated y-Butyrolactones Starting from L-Tartaric Acid: Application to Formal and Total Synthesis of Natural Products, J. Org. chem., vol. 62, p. 4007 (1997).

Bloch, R., et al., Synthesis of Both Enantiomers of y-Substituted a,B-Unsaturated y-Lactones, J. Org. Chem., vol. 52, p. 4603 (1987).

Naoshima, Y., et al., Synthesis of Racemates and (+)-Enantiomrs of y-Caprolactone, y-Dodecanolactone and s-Hexadecanolactone, Lactonic Sex Pheromones of the Dermestid Beetle, Rove Bettle and Oriental Hornet, Agric. Biol. Chem., vol. 47, p. 1431 (1983).

Solladie, G., et al., Asymmetric Synthesis of Five- and Six-Membered Lactones from Chiral Sulfoxides: Application to the Asymmetric Synthesis of Insect Pheromones, (R)-(+)-s-n-Hexadecanolactone and (R)-(+)-y-n-Dodecanolactone, J. Org. Chem., vol. 47, p. 91 (1982).

Ma, S., et al., Synthesis of B-Halobutenolides and Their Pd())-Catalyzed Cross-Coupling Reactions with Terminal Alkynes and Organozinc Reagents. A General Route to b-Substituted Butenolides and Formal Synthesis of cis-Whisky Lactone, Tetrahedron, vol. 55, p. 12137 (1999).

Nishikori, H., et al., A short-step synthesis of trans-whisky lactone by an asymmetric Michael reaction, Tetrahedron: Asymmetry, vol. 9, p. 1165 (1998).

Tsuboi, S., et al., Highly Enantioselective Synthesis of Both Enantiomers of y-Substituted Butenolides by Bakers' Yeast Reduction and Lipase-Catalyzed Hydrolysis. Total Synthesis of (3AS,6aS)-Ethisolide, Whisky Lactone, and (−)-Aveenaciolide, J. Org. Chem., vol. 63, p. 1102 (1998).

Takahata, H., et al., Concise Syntheses of Natural y-Butyrolactones, (+)-trans-Whisky Lactone, (+)-Nephrosteranic Acid, and (+)-Roccellaric Acid Using Novel Chiral Butenolide Synthons, J. Org. Chem., vol. 60, p. 5628 (1995).

Okamoto, K., et al., Production of y-Lactones by the Brown-Rot Basidiomycete *Piptoporus soloniensis*, J. Biosci. Bioeng., vol. 94, p. 182 (2002).

Bendall, J., et al., Aroma Compounds of Fresh Milk from New Zealand Cows Fed Different Diets, J. Agric. Food Chem., vol. 49, p. 4825 (2001).

Araki, S., et al., Indium in Organic Synthesis: Indium-Mediated Allylation of Carbonyl Compounds, J. Org. Chem., vol. 53, p. 1831-1833 (1988).

Ito, K., et al., Chiral Bipyrindine and Biquinoline Ligands: Their Asymmetric Synthesis and Application ot the Synthesis of trans-Whisky Lactone, Tetrahedron, vol. 52(11), p. 3905-3920 (1996).

Han, X., et al., A Short Catalytic Enantioselective Synthesis of the Vascular Antiinflammatory Eicosanoid (11R,12S)-Oxidorarachidonic Acid, J. Org. Letts., vol. 2(22), p. 3437-3438.

Bando, T., et al, Efficient Synthesis of 2-Vinyl-gamma-butyrolactones and 2-Vinyl-gamma-butyrolactams by Palladium -Catalyzed Decarboxylative Carbonylation, Bulletin of the Chemical Society of Japan. vol. 65, No. 1, pp. 97-110 (1992).

Blandin, V., et al, Asymmetric Hydrogenation of 2,4-Dioxo Esters; Selective Synthesis of 2-Hydroxy-4-oxo Esters and Direct Access of Chiral 2-Hydroxy-4-butyrolactones, European Journal of Organic Chemistry, (Aug. 1999). pp. 1787-1793.

Bryan, V. et al, Indium Mediated Intramolecular Carbocyclization in Aqueous Media. A Facile and Stereoselective Synthesis of Fused alpha-Methylene-gamma-butyrolactones, Tetrahedron Letters, vol. 37, No. 30, pp. 5341-5342 (1996).

Kiegiel, J., et al, A new asymmetric route to synthetically useful gamma-substituted gamma-butyrolactones, Tetrahedron Letters, vol. 41, pp. 4003-4006 (2000).

Leroy, B., et al, Efficient and connective synthesis of substituted butyrolactones and exo-methylene butyrolactones, Tetrahedron Letters, vol. 41, pp. 10215-10218 (2000).

Takahata, H., et al, Functionalized Chiral gamma-butyrolactones as C5 Building Units: A Straightforward Formal Synthesis of (+)-exo- and (+)-endo-Brevicomines, Tetrahedron: Asymmetry, vol. 7, No. 7, pp. 2093-2098, (1996).

* cited by examiner

PROCESS FOR PREPARING FUNCTIONALIZED γ-BUTYROLACTONES FROM MUCOHALIC ACID

This application claims the benefit of priority to U.S. provisional application Ser. No. 60/407,019 filed Aug. 29, 2002 and U.S. provisional application Ser. No. 60/449,181 filed Feb. 21, 2003.

FIELD OF THE INVENTION

The invention relates to a process for preparing functionalized γ-butyrolactones from mucohalic acids that employs a metal-mediated Barbier-type reaction. The product γ-butyrolactones is useful for preparing a variety of biologically active compounds.

BACKGROUND OF THE INVENTION

Most processes that employ the use of chemicals have the potential to cause harm to the environment. Indeed, the recognition that many of the chemical processes that are essential to the development of many modem conveniences—such as pharmaceuticals, consumer products, or transportation or communication devices—may have a harmful effect on the environment, has lead to the rise of the technological field known as "Green Chemistry." The mandate of Green Chemistry is to design, develop, and implement chemical processes and products that reduce or eliminate substances hazardous to human health and the environment. So critical is the achievement of Green Chemistry's mandate that the National Academy of Sciences established a Green Chemistry Awards program in 1995. The Green Chemistry Awards represent a competitive effort to promote chemical products and manufacturing processes that prevent pollution yet are economically viable.

One goal of Green Chemistry is to minimize or eliminate the use of solvents that are incompatible with the environment. This has lead to the use of water or other environmentally compatible solvents in some chemical processes, and to the search for substrates, reagents and reactions that are compatible with water. We identified mucohalic acid 1 (mucochloric acid (2,3-dichloro-4-oxo-2-butenoic acid) and mucobromic acid 1 (2,3-dibromo-4-oxo-2-butenoic acid), as promising candidates for Green Chemistry processing.

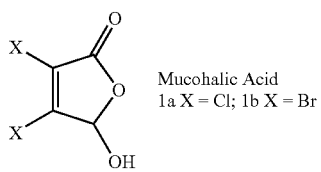

Mucohalic Acid
1a X = Cl; 1b X = Br

Mucochloric acid and mucobromic acid are commercially available and inexpensive starting materials. Both molecules are characterized by the presence of a carbon-carbon double bond with Z configuration, two halogen atoms, and two carbonyl groups. This high degree of functionality makes mucochloric and mucobromic acid particularly useful building blocks for the synthesis of a variety of biologically active heterocycles, such as substituted 1,5-dihydropyrrol-2-ones, pyrrolidines, and γ-lactams, as well as others.

Despite its great synthetic potential, however, mucohalic acid has not been commonly employed in conventional organic synthesis as a C-4 building block, let alone in "Green" organic synthesis. Presumably, this is because of the many reactive sites in the molecule, its poor stability under basic conditions, and the perception among those of ordinary skill in the art of the difficulties associated with the selective manipulation of the halogen atoms in the presence of the other functionality.

As a result, there is a need for methods or processes that allow for the selective manipulation of the functional groups present in mucolialic acid, in an environmentally compatible "Green solvent", at mild pH, atmospheric pressure, and at room temperature or lower.

SUMMARY OF THE INVENTION

These and other needs are met by the invention disclosed herein which is directed to a process for preparing functionalized γ-butyrolactones of formula I

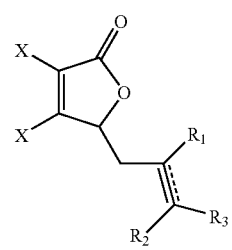

wherein X is Cl or Br, $R_1$, $R_2$, and $R_3$ are each independently H, halo, aryl, ($C_1$–$C_6$)alkoxycarbonyl, ($C_1$–$C_6$)alkanoyl, ($C_1$–$C_6$ alkyl), halo($C_1$–$C_6$ alkyl), heteroaryl($C_1$–$C_6$)alkyl or aryl($C_1$–$C_6$ alkyl), and "- - -" is a bond or is absent, provided that when "- - -" is a bond, $R_1$ and $R_2$ are absent;

comprising:

(a) contacting mucohalic acid 1 wherein X is as defined above;

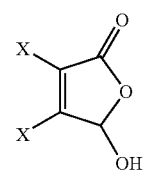

with halide 2 wherein Y is Cl, Br, or I, $R_1$, $R_2$, and $R_3$ are as defined above, and "- - -" is as defined above;

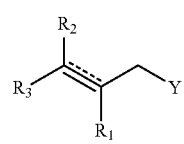

a metal selected from indium, tin or zinc; and
a catalytic amount of ammonium chloride in a solvent to form the compound of formula I.

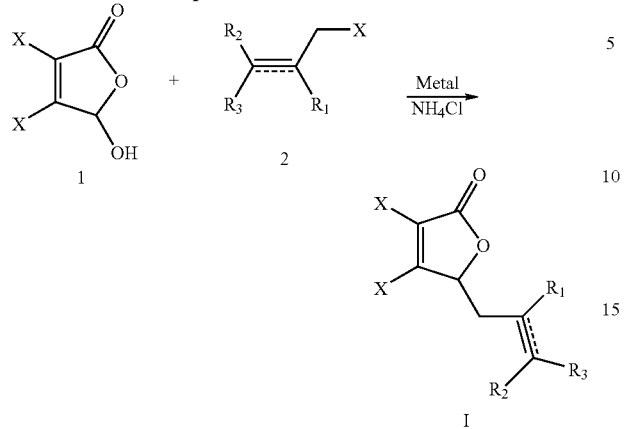

The invention process demonstrates the usefulness of mucohalic acid as a C-4 building block, particularly in the context of "Green" organic synthesis. Mucohalic acid is stable in aqueous media according to the reaction conditions of the invention process. Moreover, the hydroxyl group of mucohalic acid can be selectively manipulated in the presence of the other functionality to give high yields of product compounds.

The invention process is therefore readily adapted to the synthesis of biologically active compounds, such as those depicted in Scheme 1, particularly β- and γ amino acids.

Scheme 1

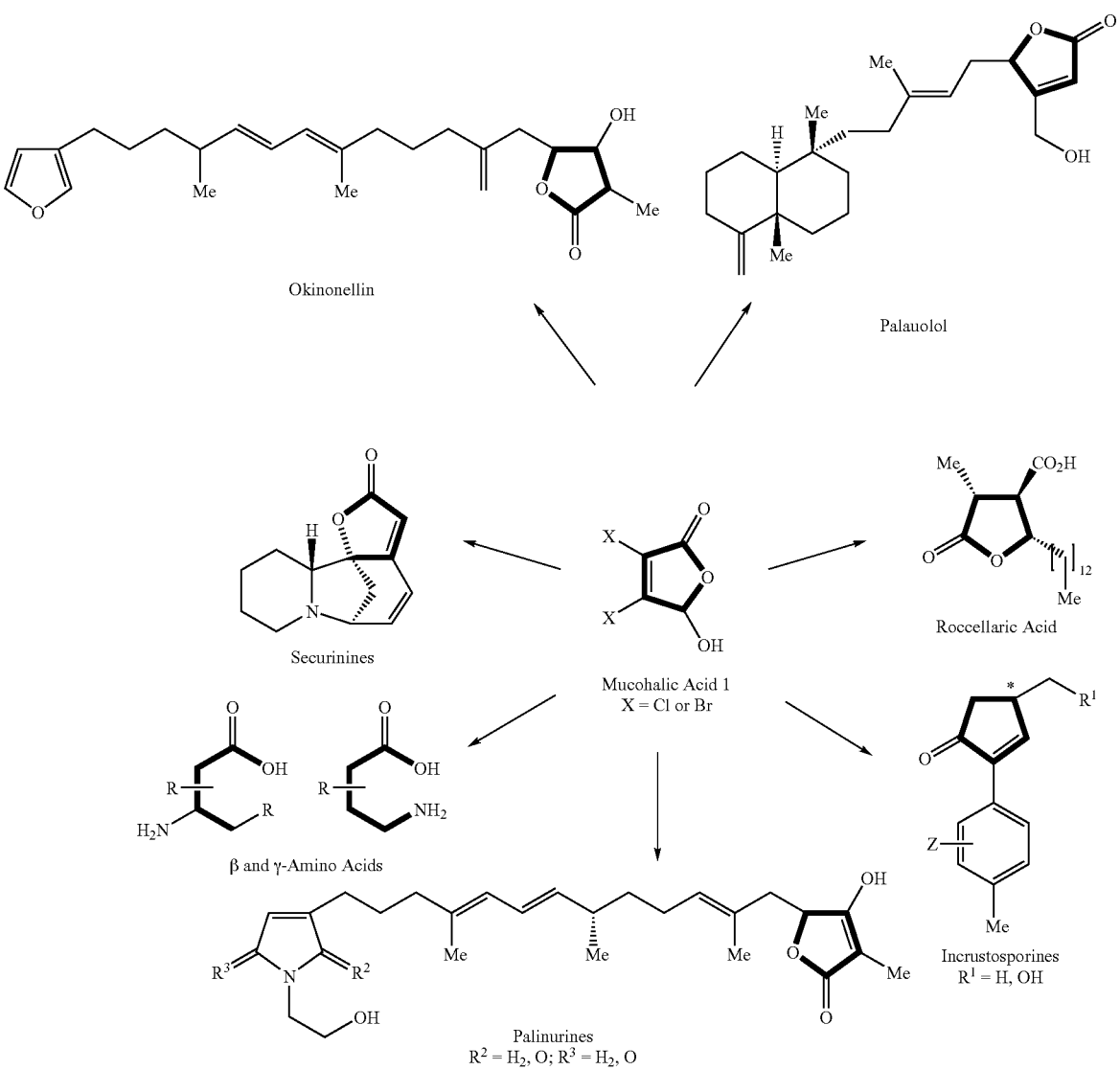

As a result, the invention also provides a process for the preparation of a compound of formula II

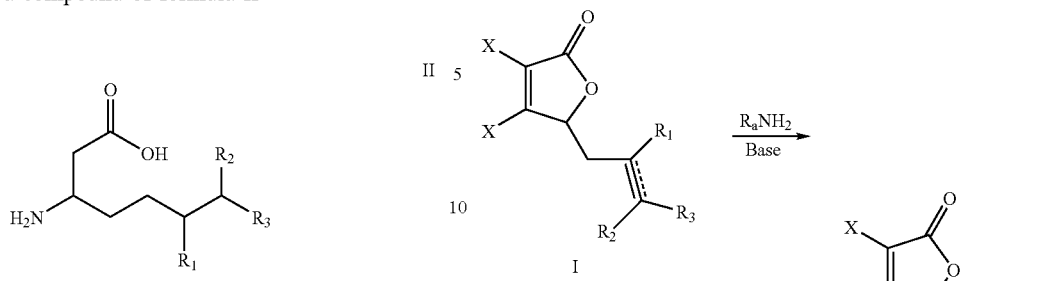

wherein $R_1$, $R_2$, and $R_3$ are each independently H, halo, aryl, $(C_1-C_6)$alkoxycarbonyl, $(C_1-C_6)$alkanoyl, $(C_1-C_6$ alkyl), halo$(C_1-C_6$ alkyl), heteroaryl$(C_1-C_6)$alkyl or aryl $(C_1-C_6$ alkyl), and comprising:

(a) contacting mucohalic acid with halide 2 wherein Y is Cl, Br, or I, $R_1$, $R_2$, and $R_3$ are as defined above, and "- - -" is a bond or is absent, provided that when "- - -" is a bond, $R_1$ and $R_2$ are absent;

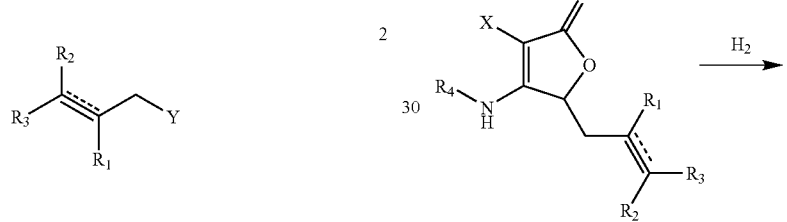

a metal selected from indium, tin or zinc; and a catalytic amount of ammonium chloride in a solvent at sufficient reaction temperature, pressure, time, and concentration to provide the γ-butyrolactone of formula I;

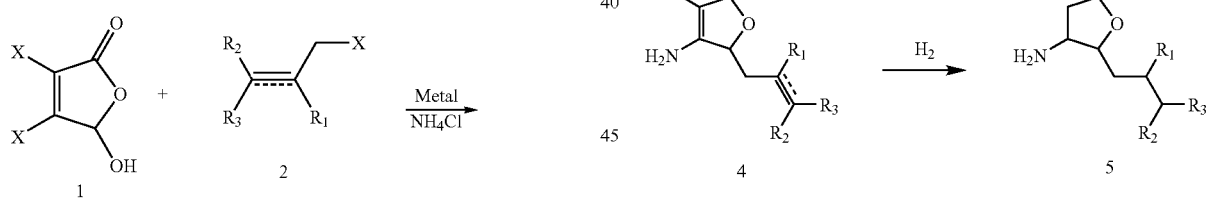

(b) reacting compound I with an amine $R_aNH_2$, wherein $R_a$ is benzyl or methylbenzyl, in the presence of base to form 3;

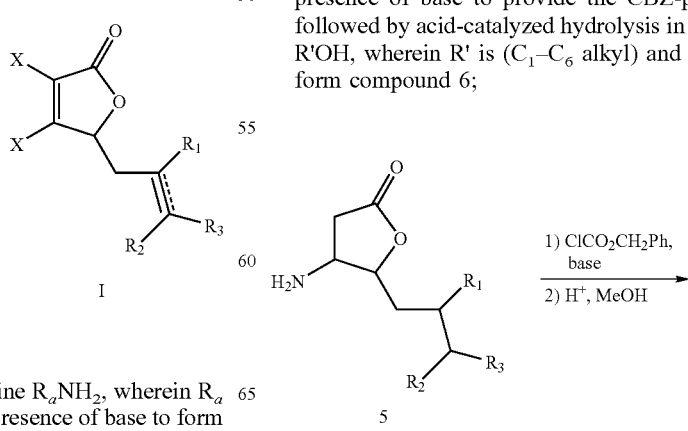

(c) hydrogenating compound 3 to initially form compound 4 and subsequently compound 5;

(d) reacting compound 5 with benzyl chloroformate in the presence of base to provide the CBZ-protected amine, followed by acid-catalyzed hydrolysis in aqueous alcohol R'OH, wherein R' is $(C_1-C_6$ alkyl) and catalytic acid to form compound 6;

-continued

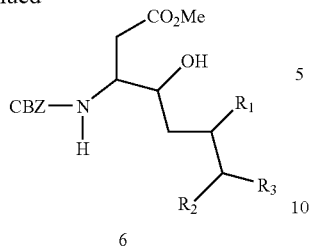

6

(e) reacting compound 6 with mesyl chloride in the presence of base, followed by treatment with NaBr of NaI, and subsequent reduction with tri-n-butyl tin hydride to form compound 7;

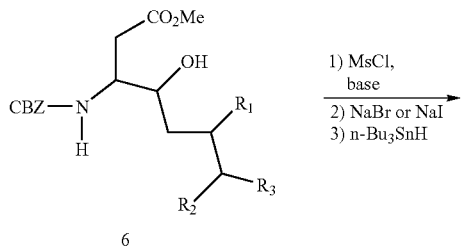

6

(f) removing the CBZ group and hydrolyzing the ester in compound 7 under acidic conditions to provide a compound of formula II.

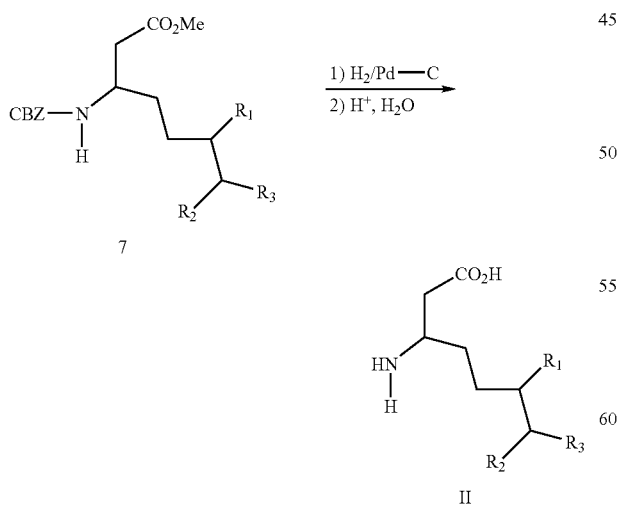

The invention also provides a process for the preparation of a compound of formula III

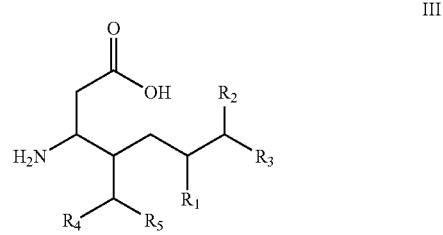

wherein $R_1$, $R_2$, and $R_3$ are each independently H, halo, aryl, $(C_1–C_6)$alkoxycarbonyl, $(C_1–C_6)$alkanoyl, $(C_1–C_6$ alkyl), halo$(C_1–C_6$ alkyl), heteroaryl$(C_1–C_6)$alkyl or aryl $(C_1–C_6$ alkyl), and $R_4$ and $R_5$ are each independently H, aryl, heteroaryl, or $(C_1–C_6$ alkyl);

comprising:

(a) contacting mucohalic acid with halide 2 wherein Y is Cl, Br, or I, $R_1$, $R_2$, and $R_3$ are as defined above, and "- - -" is a bond or is absent, provided that when "- - -" is a bond, $R_1$ and $R_2$ are absent;

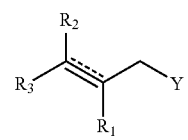

a metal selected from indium, tin or zinc; and a catalytic amount of ammonium chloride in a solvent at sufficient reaction temperature, pressure, time, and concentration to provide γ-butyrolactone I;

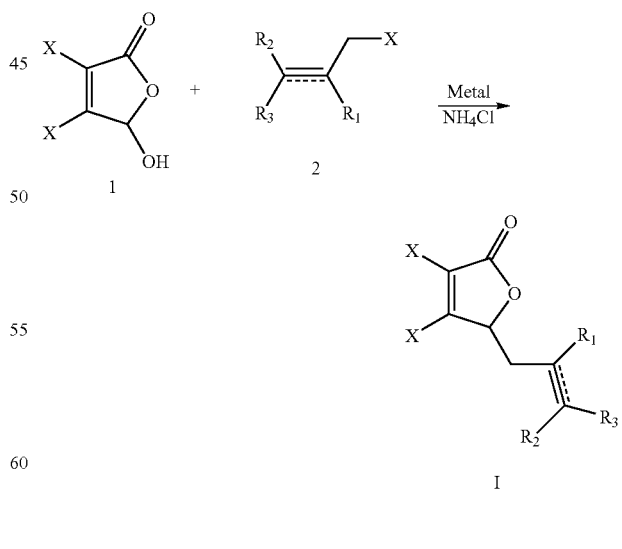

(b) reacting compound I with an amine $R_aNH_2$, wherein $R_a$ is benzyl or methylbenzyl, in the presence of base to form 3;

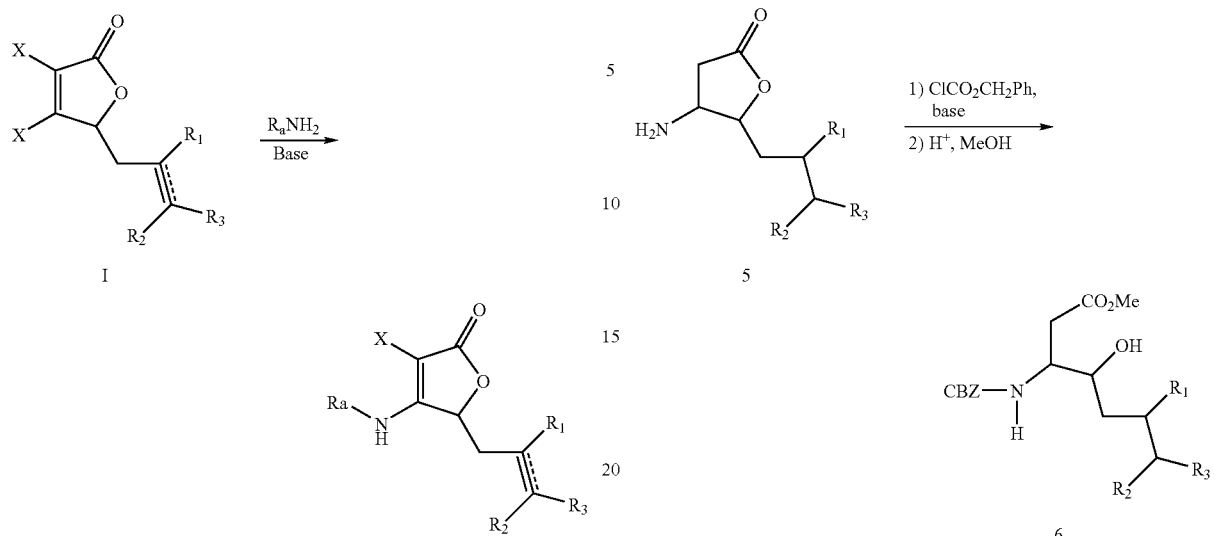

(c) hydrogenating compound 3 to initially form compound 4 and subsequently compound 5;

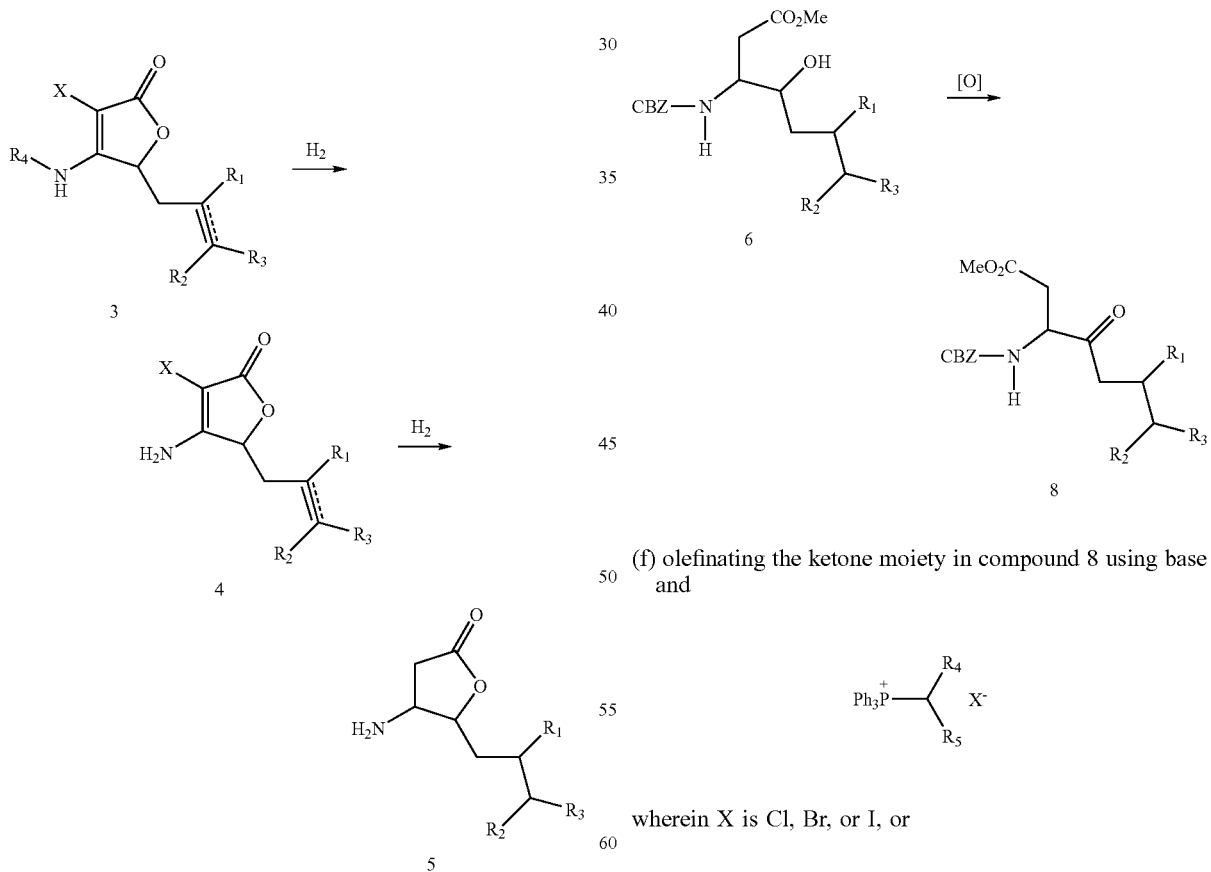

(d) reacting compound 6 with benzyl chloroformate in the presence of base to provide the CBZ-protected amine, followed by acid-catalyzed hydrolysis in methanol to form compound 7;

(e) oxidizing the alcohol moiety in compound 7 to provide compound 8;

(f) olefinating the ketone moiety in compound 8 using base and

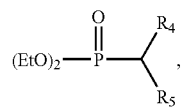

wherein X is Cl, Br, or I, or $$(EtO)_2 - \overset{\overset{O}{\|}}{P} - \overset{R_4}{\underset{R_5}{\text{C}}},$$

wherein $R_4$ and $R_5$ are as defined above to provide compound 9;

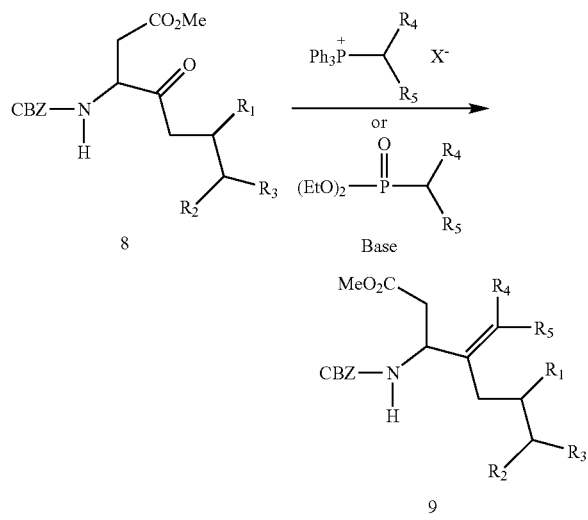

(g) hydrogenating compound 9 to provide the compound of formula III.

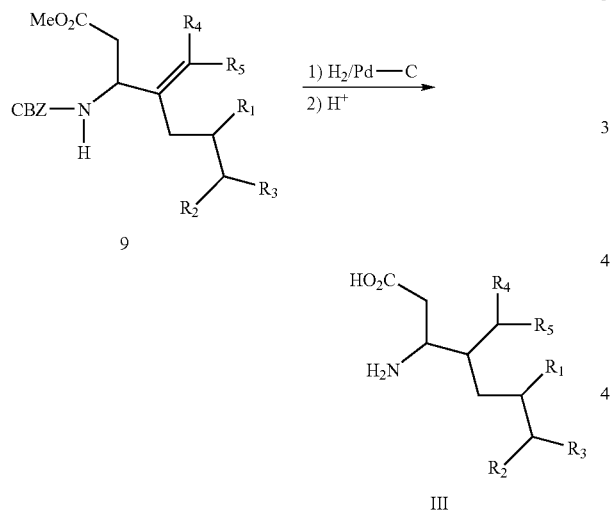

The invention also provides a process for the preparation of a compound of formula IV

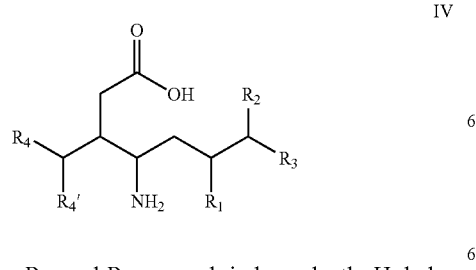

wherein $R_1$, $R_2$, and $R_3$ are each independently H, halo, aryl, $(C_1-C_6)$alkoxycarbonyl, $(C_1-C_6)$alkanoyl, $(C_1-C_6$ alkyl), halo$(C_1-C_6$ alkyl), heteroaryl$(C_1-C_6)$alkyl or aryl $(C_1-C_6$ alkyl), and $R_4$ and $R_{4'}$ are each independently H, aryl, heteroaryl, or $(C_1-C_6$ alkyl);

comprising:

(a) contacting mucohalic acid with halide 2 wherein Y is Cl, Br, or I, $R_1$, $R_2$, and $R_3$ are as defined above, and "- - -" is a bond or is absent, provided that when "- - -" is a bond, $R_1$ and $R_2$ are absent;

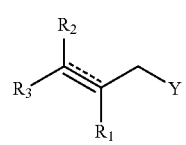

a metal selected from indium, tin or zinc; and a catalytic amount of ammonium chloride in a solvent at sufficient reaction temperature, pressure, time, and concentration to provide γ-butyrolactone I;

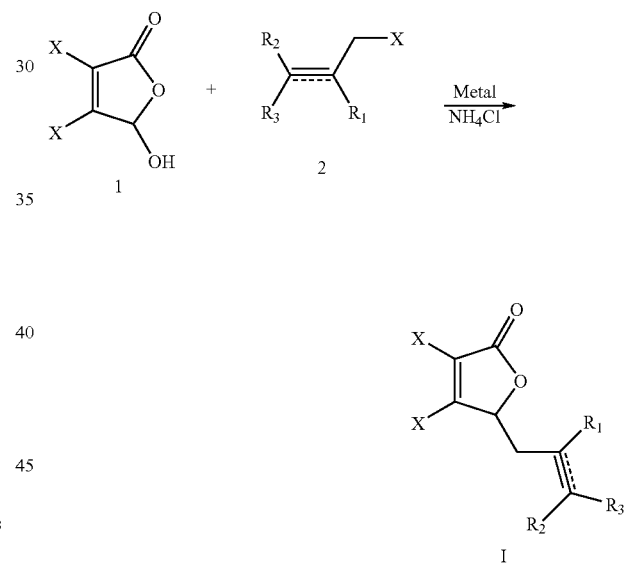

(b) adding $R_4R_{4'}CM_0$ wherein $R_4$ and $R_{4'}$ are as defined above and wherein $M_0$ is MgBr, CuBr, or $B(OH)_2$, to I, to provide 10;

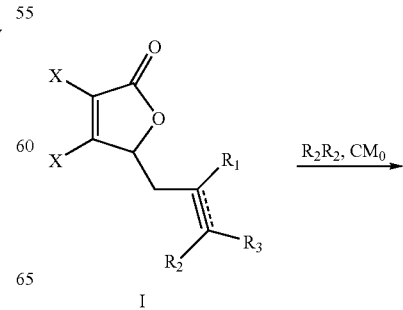

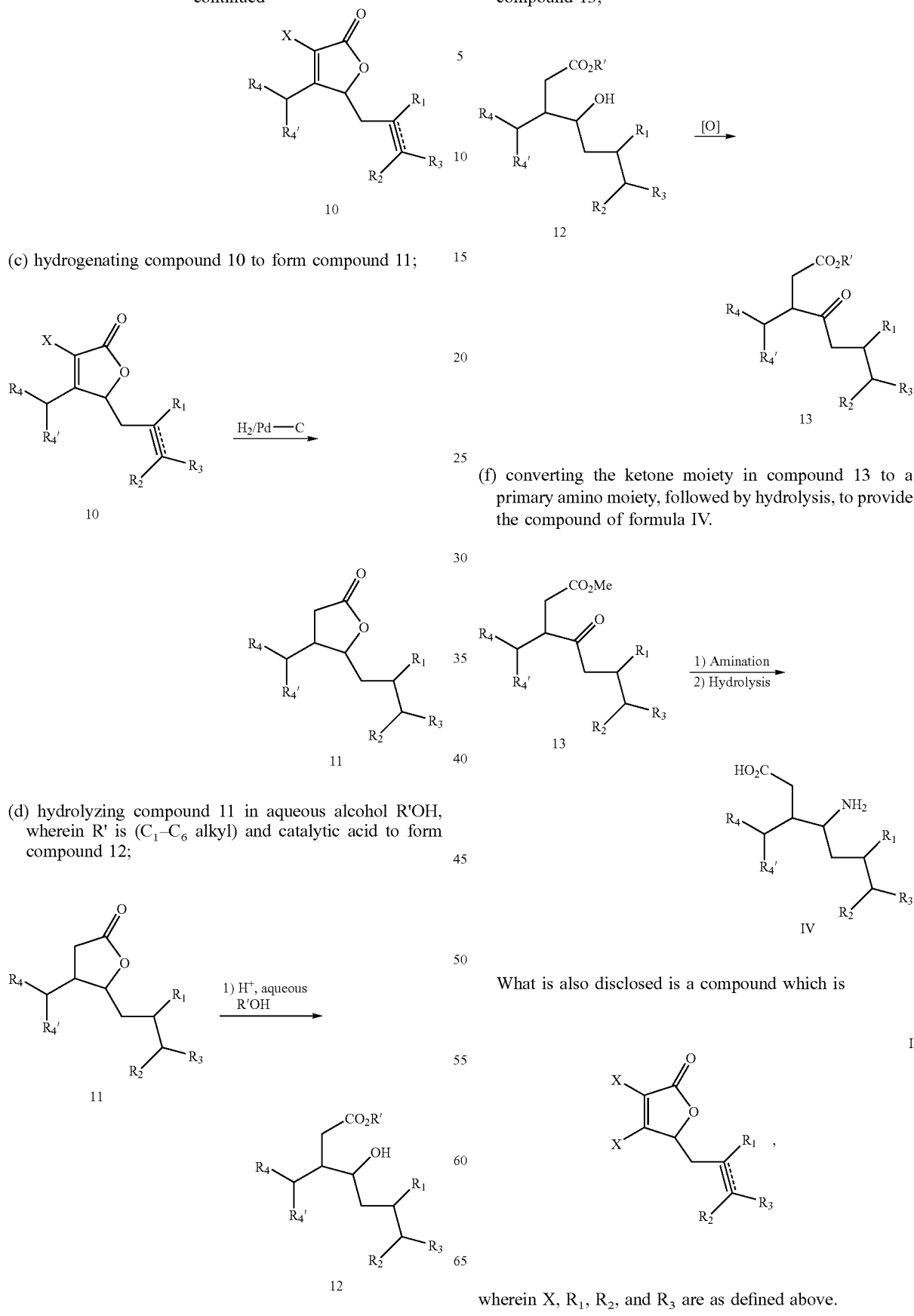

(c) hydrogenating compound 10 to form compound 11;

(d) hydrolyzing compound 11 in aqueous alcohol R'OH, wherein R' is ($C_1$–$C_6$ alkyl) and catalytic acid to form compound 12;

(e) oxidizing the alcohol moiety in compound 12 to provide compound 13;

(f) converting the ketone moiety in compound 13 to a primary amino moiety, followed by hydrolysis, to provide the compound of formula IV.

What is also disclosed is a compound which is wherein X, $R_1$, $R_2$, and $R_3$ are as defined above.

What is also disclosed is a compound which is

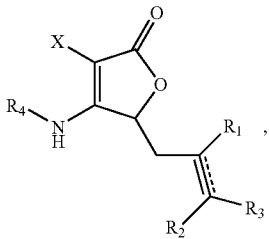

wherein X, $R_1$, $R_2$, and $R_3$ are as defined above.

What is also disclosed is a compound which is

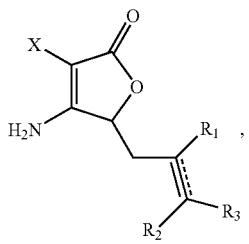

wherein X, $R_1$, $R_2$, and $R_3$ are as defined above.

What is also disclosed is a compound which is

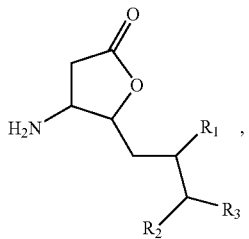

wherein $R_1$, $R_2$, and $R_3$ are as defined above.

What is also disclosed is a compound which is

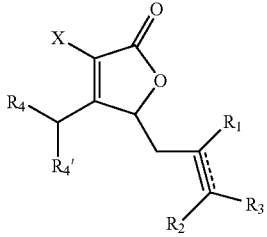

wherein X, $R_1$, $R_2$, $R_3$, $R_4$, and $R_{4'}$ are as defined above.

DETAILED DESCRIPTION OF THE INVENTION

I. Definitions

The following definitions are used, unless otherwise described: halo is fluoro, chloro, bromo, or iodo. Alkyl and alkoxy, etc. denote both straight and branched groups. However, reference to an individual radical such as "propyl" embraces only the straight chain radical. A branched chain isomer such as "isopropyl" is referred to specifically. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(Y) wherein Y is absent or is H, O, $(C_1-C_4)$alkyl, phenyl or benzyl, as well as a radical of an ortho-fused bicyclic heterocycle of about eight to ten ring atoms derived therefrom, particularly a benzo-derivative or one derived by fusing a propylene, trimethylene, or tetramethylene diradical thereto.

Specific and preferred values listed below for radicals, substituents, and ranges, are for illustration only; they do not exclude other defined values or other values within defined ranges for the radicals and substituents Specifically, "aryl" can be a cyclic or polycyclic aromatic ring having from 5 to 12 carbon atoms, and being unsubstituted or substituted with one or more of the substituent groups selected from substituents selected from alkyl, alkoxy, thioalkoxy, hydroxy, thiol, nitro, halogen, amino, $(C_1-C_6)$alkyl and $(C_1-C_6)$ dialkylamino, formyl, carboxyl, CN, —NH—CO—R, —CO—NHR, —$CO_2R$, —COR, wherein R is a $(C_1-C_6)$alkyl. Examples of aryl groups include phenyl, 2,6-dichlorophenyl, 3-methoxyphenyl, naphthyl, 4-thionaphthyl, tetralinyl, anthracinyl, phenanthrenyl, benzonaphthenyl, fluorenyl, 2-acetamidofluoren-9-yl, and 4'-bromobiphenyl, and the like.

"Heteroaryl" can be thiophene, benzothiophene, naphthothiophene, trianthrene, furan, benzofuran, isobenzofuran, pyran, chromene, xanthene, phenoxathiin, pyrrole, imidazole, pyrazole, pyridine, pyrazine, triazole, tetrazole, pyrazine, triazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, phenanthroline, phenazine, isothiazole, phenothiazine, oxazole, isoxazole, furazan, phenoxazine and the like. The heteroaryl may be unsubstituted or substituted as provided above for aryl.

"$(C_1-C_6)$alkoxycarbonyl" can be methoxycarbonyl, ethoxycarbonyl, propoxycarbonyl, isopropoxycarbonyl, butoxycarbonyl, pentoxycarbonyl, or hexyloxycarbonyl. The $(C_1-C_6)$alkoxycarbonyl may be unsubstituted or substituted as provided above for aryl.

"$(C_1-C_6)$alkanoyl" can be propanoyl, butanoyl, or the like. The $(C_1-C_6)$alkanoyl may be unsubstituted or substituted as provided above for aryl.

"$(C_1-C_6)$alkyl" can be methyl, ethyl, propyl, isopropyl, butyl, iso-butyl, sec-butyl, pentyl, 3-pentyl, hexyl or the like. The $(C_1-C_6)$alkyl group may be unsubstituted or substituted with one or more groups selected from $(C_1-C_6)$alkanoyl. alkoxy, thioalkoxy, hydroxy, thiol, nitro, halogen, amino, ($C_1$–$C_6$)alkyl and ($C_1$–$C_6$) dialkylamino, formyl, carboxyl, CN, —NH—CO—R, —CO—NHR, —$CO_2$R, —COR, wherein R is a ($C_1$–$C_6$)alkyl.

"Halo($C_1$–$C_6$)alkyl" can be iodomethyl, bromomethyl, chloromethyl, fluoromethyl, trichloromethyl, trifluoromethyl, 2-chloroethyl, 2-fluoroethyl, 2,2,2-trifluoroethyl, or pentafluoroethyl.

Aryl($C_1$–$C_6$)alkyl and heteroaryl($C_1$–$C_6$)alkyl refer to aryl or heteroaryl groups attached to a ($C_1$–$C_6$)alkyl group, wherein aryl, heteroaryl, and ($C_1$–$C_6$)alkyl are as defined herein. Examples include benzyl, methylbenzyl; i.e.,

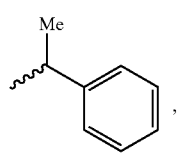

wherein "⌇⌇⌇" indicates an attachment point, 2-, 3-, and 4-methylpyridyl and the like.

The compounds prepared by the invention process may have one or more chiral centers and may exist in and be used or isolated in optically active and racemic forms. It is to be understood that the processes of the present invention can give rise to any racemic or optically-active forms, or mixtures thereof. It is to be further understood the products of the invention process can be isolated as racemic, enantiomeric, or diastereomeric forms, or mixtures thereof. Purification and characterization procedures for such products are known to those of ordinary skill in the art, and include recrystallization techniques, as well as chiral chromatographic separation procedures as well as other methods.

II. Invention Process

In one embodiment, the invention process is summarized in Scheme 2. Thus, in an aqueous medium, mucohalic acid 1 is combined with an allylic or propargylic halide 2 in the presence of a metal such as indium, tin, or zinc, and ammonium chloride, to provide the coupled product I. The skilled practitioner will recognize the transformation depicted in Scheme 1 as a Barbier-type Grignard reaction. The "Green" variant of the Barbier reaction (i.e., as performed in aqueous media) was first reported in 1991. Li, C-J.; Chan, T-H. *Tetrahedron* 1999 55, 1149–1176. To date, however, there have been no reports disclosing the densely functionalized mucohalic acid as the substrate for the Green variant of the Barbier reaction, ostensibly because of its perceived high reactivity and poor stability.

Scheme 2

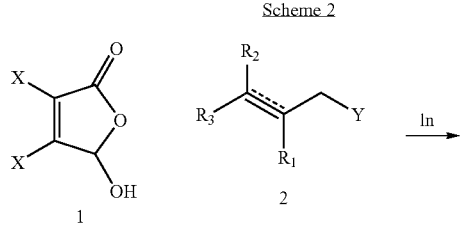

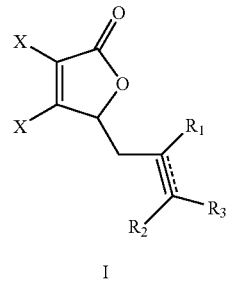

A. Reagents

1. Mucohalic Acid

Either mucobromic or mucochloric acid are suitable for use in the Green variant of the Barbier reaction of the present invention.

2. Allyl or Propargyl Halide

As depicted above, the mucohalic acid 1 is combined with allylic or propargylic halide 2 in the invention process. When "- - -" is absent in halide 2, the skilled practitioner will recognize that compound 2 is an allylic halide wherein all of $R_1$, $R_2$, and $R_3$ are present. When "- - -" is a bond in halide 2, the skilled practitioner will recognize that compound 2 is a propargylic halide, wherein $R_1$ and one of $R_2$ or $R_3$ is absent.

A wide variety of allyl or propargyl halides may be used in the invention process. Referring to Scheme 1, Y in allyl or propargyl halide 2 may be Cl, Br, or I. $R_1$, $R_2$, and $R_3$ each independently may be H, halo, aryl, ($C_1$–$C_6$)alkoxycarbonyl, ($C_1$–$C_6$)alkanoyl, or ($C_1$–$C_6$ alkyl) and "- - -" is a bond or is absent, provided that when "- - -" is a bond, $R_1$ and $R_2$ are absent.

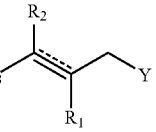

a. Allylic Halide

In one embodiment of the invention process, when compound 2 is an allylic halide (i.e., "- - -" is absent), at least one of $R_1$ $R_2$, and $R_3$ is H and the others of $R_1$ $R_2$, and $R_3$ are each independently halo, aryl, ($C_1$–$C_6$)alkoxycarbonyl, ($C_1$–$C_6$)alkanoyl, or ($C_1$–$C_6$ alkyl).

In another embodiment, $R_1$ is H, and one of $R_2$ and $R_3$ is H, while the other of $R_2$ and $R_3$ is halo, aryl, ($C_1$–$C_6$) alkoxycarbonyl, ($C_1$–$C_6$)alkanoyl, or ($C_1$–$C_6$ alkyl).

In another embodiment, $R_1$ is aryl, ($C_1$–$C_6$)alkoxycarbonyl, ($C_1$–$C_6$)alkanoyl, or ($C_1$–$C_6$ alkyl), and at least one of $R_2$ and $R_3$ is H.

b. Propargylic Halide

In another embodiment of the invention process, when compound 2 is a propargylic halide (i.e., "- - -" is a bond), $R_1$ and $R_2$ are absent, and $R_3$ is H.

In another embodiment, $R_3$ is aryl, ($C_1$–$C_6$)alkoxycarbonyl, ($C_1$–$C_6$)alkanoyl, or ($C_1$–$C_6$ alkyl).

3. Metal

A metal is used to mediate the invention process. Preferred metals are indium, tin, or zinc.

2. Procedure and Stochiometry

In one variant of the invention process, mucohalic acid 1 is contacted with halide 2, a metal such as indium, tin, or zinc, and ammonium chloride in a solvent. "Contacted" means that the reaction components are typically mixed in a liquid to form a homogeneous or heterogeneous mixture. The liquid employed in the present invention is selected from a polar protic or polar aprotic solvent, in the presence or absence of water. The polar protic solvent is an alcohol such as methanol or ethanol, or the like. The polar aprotic solvent is selected from tetrahydrofuran, DMPU, or the like. Typically, when water is used as a cosolvent for the invention process, it is used in equal volume with the polar protic or aprotic solvent to achieve the desired reaction concentration. For example, when water is used as a cosolvent with THF, the volume ratio of water to THF is approximately 1:1.

Alternatively, a "room temperature ionic liquid" (RTIL) may be used as the solvent for the invention process. Such RTILs include [bmim][BF$_4$], [bmim][PF$_6$], [bmim][Tf$_2$N], where bmim is 1-butyl-3-methylimidazolium and Tf is CF$_3$SO$_2$. See Gordon, C. M., *Green Chemistry*, 2002, 4, 124–128.

In one embodiment of the invention process, the molar equivalents of each of the reaction components (i.e., mucohalic acid, allylic or propargylic halide, indium, and ammonium chloride) used in the invention process are:

about 1 equivalent of compound of mucohalic acid 1;
about 1.0 to about 1.5 equivalents of halide 2;
about 1.0 to about 1.5 equivalents of indium; and
about 0.1 to about 0.5 equivalents of ammonium chloride.

In another embodiment of the invention process, the molar equivalents of each of the reaction components used in the invention process are:

about 1 equivalent of the compound of mucohalic acid 1;
about 1.1 to about 1.3 equivalents of halide 2;
about 1.1 to about 1.3 equivalents of indium; and
about 0.1 to about 0.3 equivalents of ammonium chloride.

In another embodiment of the invention process, the molar equivalents of each of the reaction components used in the invention process are:

about 1 equivalent of the compound of mucohalic acid 1;
about 1.2 equivalents of halide 2;
about 1.2 equivalents of indium; and
about 0.1 to about 0.2 equivalents of ammonium chloride.

The mucohalic acid, allylic or propargylic halide, metal, and ammonium chloride are mixed in the solvent, for instance, by magnetic or mechanical stirring, at a temperature of about 0 to about 50° C. More preferably, the temperature is about 10 to about 40° C. More preferably, the temperature is about 20 to about 30° C. Even more preferably, the temperature is about 22 to about 27° C.

The invention process is typically run at atmospheric pressure, or about 1 atmosphere of pressure.

The mucohalic acid, allylic or propargylic halide, metal, and optional ammonium chloride are mixed in the solvent at the designated concentration, temperature, and pressure, for a time sufficient to maximize conversion of mucohalic acid to product I, while minimizing of side reactions and the formation of undesired by-products and decomposition products. Typical reaction times for the process are in the range of about 10 to 60 hours. More typically reaction times are in the range of about 12 to about 50 hours, and more typically, in the range of about 14 to 20 hours.

To demonstrate the present invention process, the reaction of mucochloric acid and mucobromic acid with allyl bromide in the presence of indium in THF/water was investigated (Table 1). The reactions were conducted at room temperature over the course of 16 hours. Initially, lactone 14 was isolated in 90% yield when X=Cl; when X=Br, the yield was 70% (in THF/water) and 86% (in MeOH/water).

TABLE 1

Reaction of Mucohalic Acid with Allyl Bromide.[a]

1a X = Cl
1b X = Br

14a X = Cl
14b X = Br

| entry | Mucohalic Acid | Solvent | Yield (%) |
| --- | --- | --- | --- |
| 1 | 1a | 1:1 THF/Water | 90 |
| 2 | 1b | 1:1 THF/Water | 70 |
| 3 | 1b | 1:1 MeOH/Water | 86 |

[a]Reaction conditions for entries 1, 2 and 3: 1 equiv of mucohalic acid, 1.2 equiv. of allyl bromide, 0.1 equiv of NH$_4$Cl, for 16 h. The reaction time was not optimized. Products were isolated and purified by silica gel chromatography and/or crystallization. Products are estimated to be >95% pure by $^1$H NMR and elemental analysis. All compounds gave satisfactory elemental analysis data.

The invention process has been further extended to both electron rich or poor allylic or propargylic systems (Table 2). Thus, electron rich cinnamyl bromide (Entry 3) underwent reaction with mucochloric acid to provide a mixture of allyated products in 46% yield. Electron-deficient methyl (2-bromomethyl) acrylate (Entries 2 and 6) underwent reaction with mucochloric or mucobromic acid to provide the allylated products 76 and 74% yields, respectively. Propargyl bromide (Entry 8) underwent reaction with mucobromic acid to provide a mixture of products in 36% yield.

TABLE 2

Reaction of Mucohalic Acid with Different Allyl and Propargyl Halides.[a]

$$\text{1a X = Cl} \quad \text{1b X = Br}$$

mucohalic acid + "allyl or propargyl halide" →(In, NH$_4$Cl / Solvent) product

| Entry | Mucohalic Acid | "Allyl or propargyl halide" | Product | Yield (%) |
|---|---|---|---|---|
| 1 | 1a | Allyl Bromide | 3,4-dichloro-5-allyl-furanone | 90 |
| 2 | 1a | Methyl (2-bromomethyl) Acrylate | 3,4-dichloro-5-(2-(methoxycarbonyl)allyl)-furanone | 76 |
| 3 | 1a | Cinnamyl Bromide | linear (E)-cinnamyl and branched α-phenylallyl isomers | 46 |
| 4 | 1a | 3-Bromo-2-methylpropene | 3,4-dichloro-5-(1-methylallyl)-furanone | 82 |
| 5 | 1b | Allyl Bromide | 3,4-dibromo-5-allyl-furanone | 86 |

TABLE 2-continued

Reaction of Mucohalic Acid with Different Allyl and Propargyl Halides.[a]

1a X = Cl
1b X = Br

| Entry | Mucohalic Acid | "Allyl or propargyl halide" | Product | Yield (%) |
|---|---|---|---|---|
| 6 | 1b | Methyl (2-bromomethyl) Acrylate | (structure with X, X, CO₂Me) | 74 |
| 7 | 1b | Methyl (2-Bromomethyl) Acrylate | (structure with Br, Br, Me) | 61 |
| 8 | 1b | Propargyl Bromide | (two structures: allene and propargyl) | 36 |

[a] 1 equiv of mucohalic acid, 1.2 equiv. of allyl bromide, 0.1 equiv of $NH_4Cl$, for 16 h. The reaction time was not optimized. Products were isolated and purified by silica gel chromatography and/or crystallization. Products are estimated to be >95% pure by $^1H$ NMR and elemental analysis. All compounds gave satisfactory elemental analysis data.

Indium was successfully replaced with much less expensive tin with no reduction in product yield, as summarized in Table 3. See also Wang, Z.; Zha, Z.; Zhou, C. *Org. Lett.* 2002, 4, 1683.

TABLE 3

Tin Mediated Allylation of Mucohalic Acids[a]

[Scheme: X-substituted furanone (1a X = Cl; 1b X = Br) + allylic bromide → product, conditions: Sn, THF/H₂O, NH₄Cl (cat.)]

| entry | s.m. | allylic bromide | product | yield (%)[b] |
|---|---|---|---|---|
| 1 | 1a | allyl bromide | 3,4-dichloro-5-allyl furanone (8) | 84 |
| 2 | 1a | allyl bromide | 3,4-dichloro-5-allyl furanone (8) | 77[c] |
| 3 | 1a | methallyl bromide | 3,4-dichloro-5-methallyl furanone (8) | 50 |
| 4 | 1b | allyl bromide | 3,4-dibromo-5-allyl furanone (12) | 75 |
| 5 | 1b | methallyl bromide | 3,4-dibromo-5-methallyl furanone (12) | 41 |
| 6 | 1b | prenyl bromide | 3,4-dibromo-5-prenyl furanone (12) | NR |

[a]Reaction conditions: 1 equiv of 1a or 1b, 1.2 equiv of tine metal, 1.2 equiv of desired allyl bromide, NH₄Cl (cat.), 1:1 v/v H₂O/THF, 24–48 h at room temperature. The reaction time was not optimized.
[b]Products were isolated and purified by silica gel chromatography and/or crystallization. Products are estimated to be >95% pure by ¹H NMR and elemental analysis. All compounds gave satisfactory elemental analysis data.

III. Demonstration of Invention Process in Synthesis

The invention process disclosed herein allows for convenient synthetic access to a number of biologically active compounds. This section describes synthetic routes to several of compounds depicted in Scheme 1.

A. β-Amino Acids

A number of β-amino acids bind to the alpha-2-delta subunit of a calcium channel and are thus useful in the treatment of an array of disorders. See U.S. application Ser. No. 10/401,060, filed Mar. 27, 2003.

1. Synthesis of Compounds of Formula II

An approach to β-amino acids of formula II is depicted in Scheme 3. Thus, compound 14 is prepared using mucobromic acid and allyl bromide in the presence of indium or tin using the invention process disclosed herein. Michael addition of benzyl amine or its equivalent to compound 14 occurs readily at room temperature to provide the 1,4 conjugate addition product 15. Compound 15 was hydrogenated under conventional conditions known to the skilled artisan (H₂/Pd—C) to initially provide compound 16. Submission of compound 16 to hydrogenation conditions for longer periods of time or higher temperatures or pressures can give rise to compound 17. Protection of the amine moiety in compound 17 provides compound 18. Acid catalyzed hydrolysis of lactone 18 in aqueous alcohol such as methanol can give rise to 3-hydroxy ester 19. The alcohol moiety in compound 19 is converted to the mesylate upon treatment with mesyl chloride in the presence of an amine base such as triethyl amine, which is subsequently converted to the bromide or iodide 20 upon treatment with NaBr or NaI in acetone. Barton-type reduction of 21 using nBu₃SnH, followed by deprotection and hydrolysis provides the target compound of formula IIA.

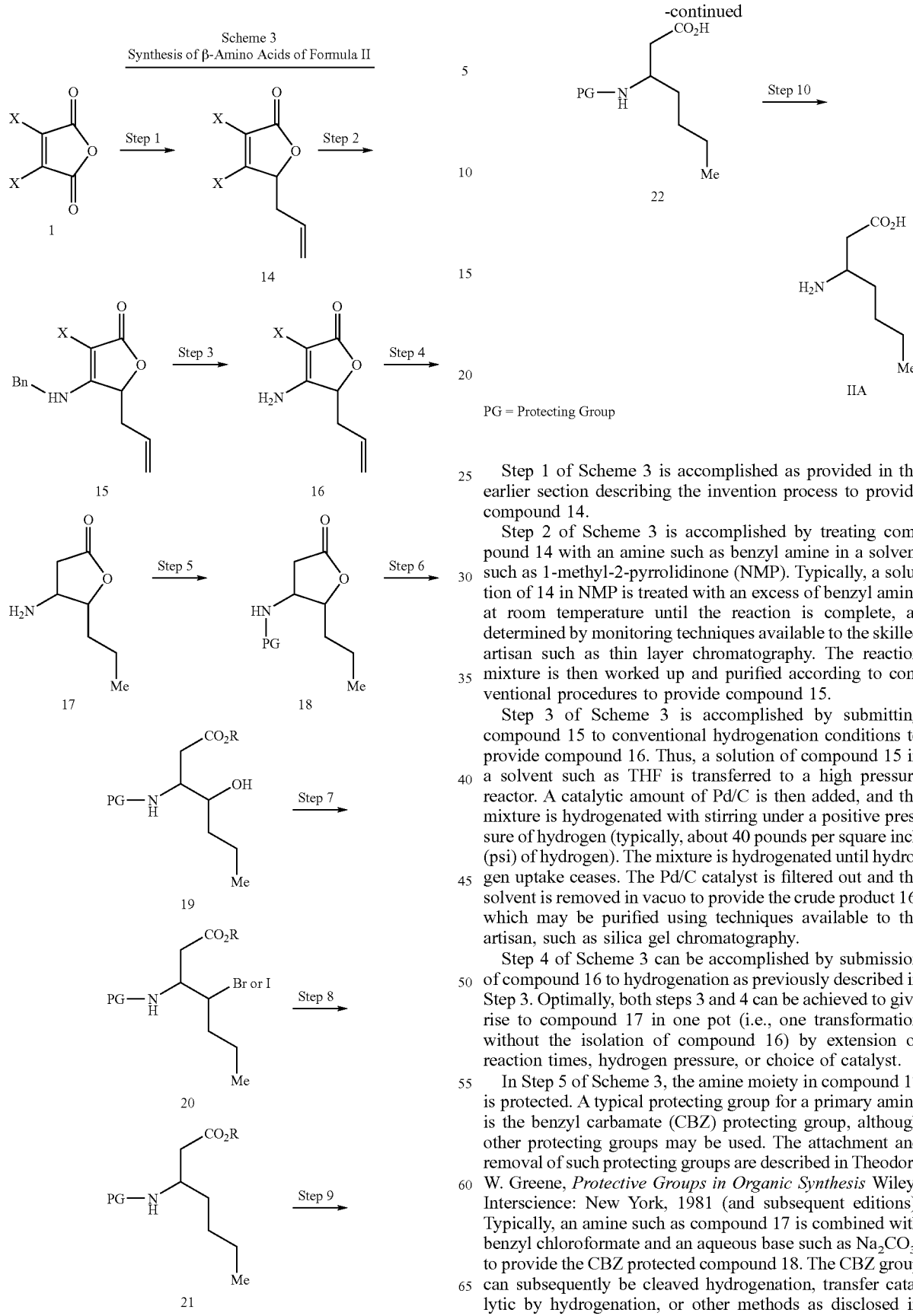

Step 1 of Scheme 3 is accomplished as provided in the earlier section describing the invention process to provide compound 14.

Step 2 of Scheme 3 is accomplished by treating compound 14 with an amine such as benzyl amine in a solvent such as 1-methyl-2-pyrrolidinone (NMP). Typically, a solution of 14 in NMP is treated with an excess of benzyl amine at room temperature until the reaction is complete, as determined by monitoring techniques available to the skilled artisan such as thin layer chromatography. The reaction mixture is then worked up and purified according to conventional procedures to provide compound 15.

Step 3 of Scheme 3 is accomplished by submitting compound 15 to conventional hydrogenation conditions to provide compound 16. Thus, a solution of compound 15 in a solvent such as THF is transferred to a high pressure reactor. A catalytic amount of Pd/C is then added, and the mixture is hydrogenated with stirring under a positive pressure of hydrogen (typically, about 40 pounds per square inch (psi) of hydrogen). The mixture is hydrogenated until hydrogen uptake ceases. The Pd/C catalyst is filtered out and the solvent is removed in vacuo to provide the crude product 16, which may be purified using techniques available to the artisan, such as silica gel chromatography.

Step 4 of Scheme 3 can be accomplished by submission of compound 16 to hydrogenation as previously described in Step 3. Optimally, both steps 3 and 4 can be achieved to give rise to compound 17 in one pot (i.e., one transformation without the isolation of compound 16) by extension of reaction times, hydrogen pressure, or choice of catalyst.

In Step 5 of Scheme 3, the amine moiety in compound 17 is protected. A typical protecting group for a primary amine is the benzyl carbamate (CBZ) protecting group, although other protecting groups may be used. The attachment and removal of such protecting groups are described in Theodora W. Greene, *Protective Groups in Organic Synthesis* Wiley-Interscience: New York, 1981 (and subsequent editions). Typically, an amine such as compound 17 is combined with benzyl chloroformate and an aqueous base such as $Na_2CO_3$ to provide the CBZ protected compound 18. The CBZ group can subsequently be cleaved hydrogenation, transfer catalytic by hydrogenation, or other methods as disclosed in Greene.

In Step 6 of Scheme 3, the lactone ring is opened in compound 18 to provide the ester 19. Typically, the substrate ester/lactone is dissolved in an alcohol such as methanol or ethanol and treated with a catalytic amount of acid at room temperature or upon gentle heating if necessary.

In Step 7 of Scheme 3, the alcohol moiety in compound 19 is converted to a leaving group such as a tosylate, mesylate, triflate, or the like, which is then converted to the bromide or iodide 20 upon treatment with NaBr or NaI in acetone. Typically, to convert an alcohol such as compound 19 to a mesylate, the alcohol is dissolved in a solvent such as methylene chloride. The resulting mixture is typically cooled using an ice bath or cooling device. Mesyl chloride and an amine base such as triethyl amine is then added to the mixture. The mixture is typically allowed to warm to room temperature and is then worked up according to procedures well known to the skilled artisan.

To convert the mesylate to bromide or iodide 20, the mesylate is treated with NaBr or NaI in acetone with gentle heating.

In Step 8 of Scheme 3, bromide or iodide 20 is reduced using tri-butyltin hydride and azobisisobutyronitrile (AIBN) to provide ester 21. The tributyltin hydride reduction reaction is well known to the skilled artisan, particularly for the radical mediated replacement of hydrogen for a halide. See, e.g., Neumann, W. *Synthesis* 1987, 665–683, and references cited therein.

In Step 9 of Scheme 3, ester 21 is hydrolyzed to acid 22. The acid catalyzed hydrolysis of esters is also a well-known transformation and typically requires the use of a catalytic amount of acid and an aqueous alcohol solvent system. The mixture of the acid catalyst and requisite ester is heated in the aqueous alcohol solvent system for sufficient time to allow for maximum conversion of the starting material to product.

In Step 10 of Scheme 3, the CBZ group is cleaved in compound 22 to provide a compound of formula IIA. As indicated for Step 5, the CBZ group is readily cleaved by hydrogenation, transfer catalytic hydrogenation, or other methods as disclosed in Greene.

2. Synthesis of Compounds of Formula III

An approach to β-amino acids of formula III is summarized in Scheme 4 and commences from compound 19 (cf. Scheme 3). Thus, alcohol 19 is oxidized to ketone 23 using a method available to the skilled artisan. Olefination of the ketone moiety in compound 23 is readily achieved upon reaction with base and a Wittig reagent or a Wittig reagent equivalent such as a phosphonate carbanion to provide compound 24. Submission of compound 24 to hydrogenation leads to cleavage of the CBZ protecting group and reduction of the double bond to afford compound 25. Acid-mediated Hydrolysis of ester 25 provides the compound of formula IIIA.

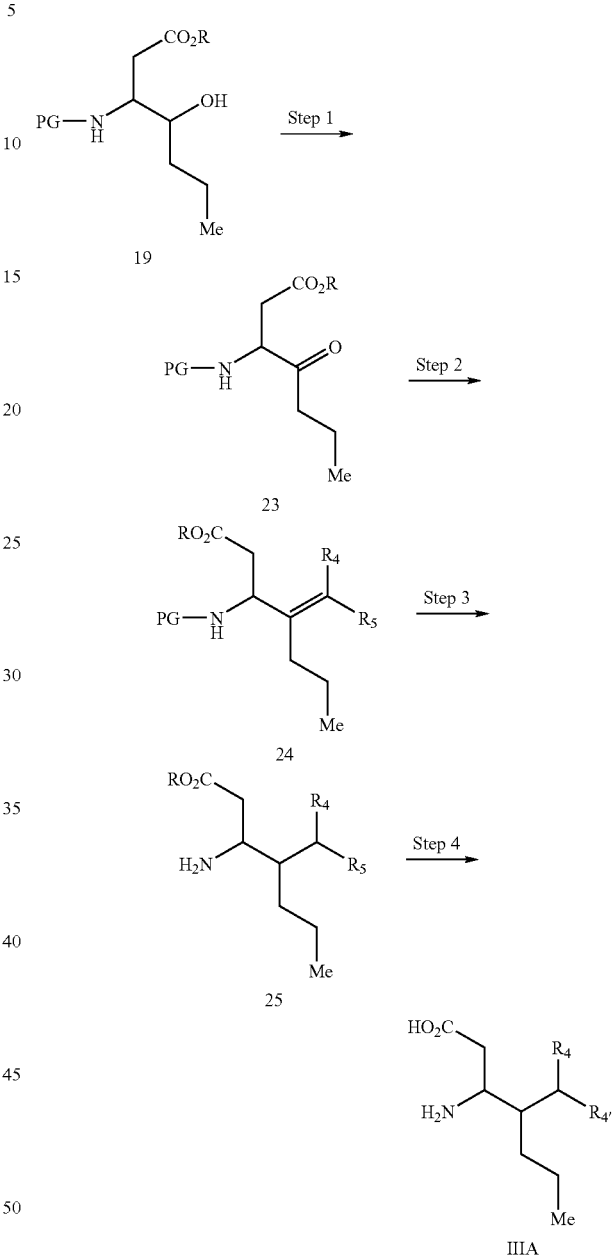

Scheme 4
Synthesis of β-Amino Acids of Formula III

In Step 1 of Scheme 4, the alcohol moiety in compound 19 is oxidized to a ketone moiety to provide compound 23. As indicated previously, the formation of a ketone from a secondary alcohol is a commonly employed reaction in organic synthesis. Stoichiometric oxidizing agents such as hypochlorite, chromium reagents (PCC and PDC), active manganese oxides, permanganate, Dess-Martin periodinane, o-iodoxybenzoic acid (IBX), and activated DMSO as in the Swern oxidation are routinely used. A number of newer oxidation methods are also available. For references for any of these methods, see Takashi Ooi, Hidehito Otsuka, Tomoya Miura, Hayato Ichikawa, and Keiji Maruoka, *Org. Lett.* 4 (16), 2669–2672, 2002.

In Step 2 of Scheme 4, the ketone moiety in compound 23 undergoes olefination in the presence of base using

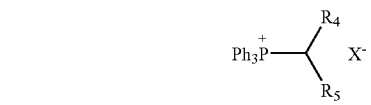

wherein X is Cl, Br, or I, or

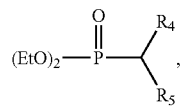

to provide compound 24. The Wittig olefination reaction is well known and commonly employed by the skilled artisan. See Francis A. Carey & Richard J. Sundberg, *Advanced Organic Chemistry, Part B* New York: Plenum 4$^{th}$ Edition, 2001, and references cited therein.

In Step 3 of Scheme 4, submission of compound 24 to hydrogenation as provided in Scheme 3, step 10, affords compound 25.

In Step 4 of Scheme 4, submission of compound 25 to hydrolysis as provided in Scheme 3, step 9, affords the compound of formula IIIA.

B. γ-Amino Acids

Gamma-amino acids such as pregabalin (S-3-Aminomethyl-5-methyl-hexanoic acid) exhibit an array of useful medicinal properties, as disclosed in WO 93/23383, as well as U.S. Pat. No. 6,306,910 and WO 00/76958, the latter two of which are assigned to the same assignee as the instant application.

Scheme 5 provides an approach to γ-amino acids of formula IV commencing from compound 14. Thus, conjugate addition of an organocuprate reagent $R_4R_{4'}CM$ to 14, followed by halide elimination, provides the substituted furanone 26. Hydrogenation of compound 26 affords compound 27. Acid catalyzed ring-opening of 27 gives rise to γ-hydroxy ester 28. Oxidation of the alcohol moiety in compound 28 provides ketone 29. Ketone 29 can be converted to amine 30 via, for example, reductive amination, or upon conversion to the oxime or imine, followed by selective reduction. Finally, compound 30 is converted to compound IVA upon ester hydrolysis.

Scheme 5
Synthesis of β-Amino Acids of Formula IV

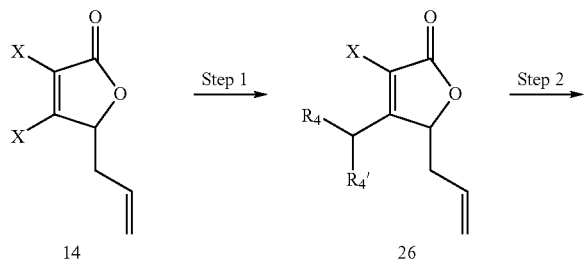

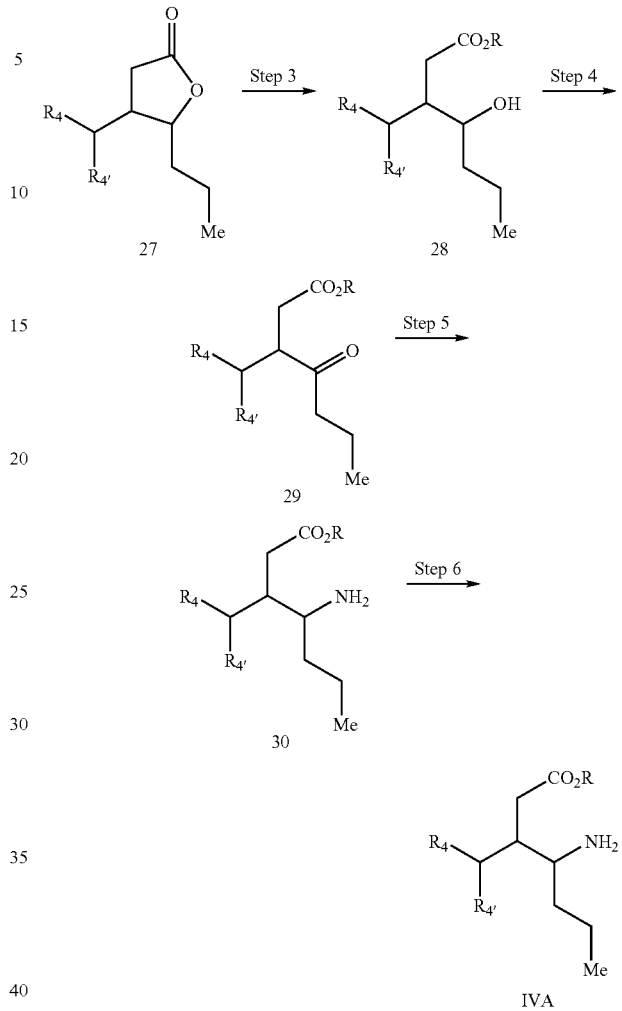

In Step 1 of Scheme 5, conjugate addition of $R_4R_{4'}CM$ to compound 14, followed by halide elimination, provides compound 26. In a typical procedure employing organocopper chemistry, the organocuprate is generated in situ in the presence of N-methypyrrolidinone (NMP) from a commercially available Grignard reagent (e.g., an alkyl- aryl-, or alkylmagnesium bromide) and copper iodide. If the requisite Grignard reagent is not commercially available, it can be readily prepared from the corresponding organohalide compound using one of the many methods available to the skilled artisan. The furanone is then added to the organocuprate reagent over 5 to 10 minutes at −10 to 0° C., and the resulting mixture is allowed to warm to room temperature, then worked up.

In Step 2 of Scheme 5, submission of compound 26 to hydrogenation as provided in Scheme 3, step 10, affords compound 27.

In Step 3 of Scheme 5, the lactone ring is opened in compound 27 to provide γ-hydroxy ester 28.

In Step 4 of Scheme 5, the alcohol moiety in compound 28 is oxidized to a ketone moiety as in Scheme 4, step 1, to provide compound 29.

In Step 5 of Scheme 5, the ketone moiety in compound 29 is converted to a primary amino moiety in compound 30 via: (i) reductive amination; (ii) conversion to the oxime followed by reduction; or (iii) conversion to the imine, followed by reduction.

A variety of conditions and reagents are available to the skilled artisan for the reductive amination of ketones to amines and are reviewed in Abdel-Magid, et. al., *J. Org. Chem.*, 1996, 61, 3849–3862. Sodium triacetoxyborohydride is generally used as the reducing agent. The amine is typically a primary amine such as benzyl amine. Typically, an excess of sodium triacetoxyborohydride is added slowly to a mixture of the ketone and benzyl amine (1.1 equivalent) in a solvent such as chloroform, generally at room temperature, until the reaction is complete to provide the benzyl-protected amine. The benzyl group is readily removed upon hydrogenation to afford compound 30.

Alternative reductive amination procedures are also available. For example, Kitamura and coworkers disclose a catalytic Leuckart Wallach-type reductive amination employing a Cp*Rh(III) and ammonium formate. Kitamura, M., et. al. *J. Org. Chem.*, 2002, 67, 8685–8687. The advantage of this approach is that it provides primary amine 30 directly.

Ketone 29 may also be converted to an oxime, which, upon reduction, provides amine 30. Procedures for oxime formation and stereoselective and non-stereoselective reduction are available at, for instance, Campos, K., et. al., *J. Org. Chem.*, 2002, 67, 8685–8687, and references cited therein. Alternatively, ketone 23 is converted to the imine and is then reduced either stereoselectively or non stereoselectively to provide the requisite amine. Procedures for the transformation are available at, for instance, Kobayashi, S.; *Chem. Rev.* 1999, 99, 1069–1094 and references cited therein.

In Step 6 of Scheme 5, submission of compound 30 to hydrolysis as provided in Scheme 3, step 9, affords the compound of formula IVA.

C. Other Biologically Active Target Compounds

We envisioned mucohalic acid as an inexpensive and convenient starting material for the synthesis of a number of other biologically active compounds, as depicted in Scheme 1, above. These include antifungal metabolites isolated from the marine sponge pachastrissa spa, lactone x, the bioactive marine natural products palinurin and palinurine A and B, the novel cytotoxic sesterterpenes from the sponge Sarcotragus, or antifungal compounds based on the fungal metabolite incrustosporinne, among others. Other synthetic targets accessible via mucohalic acid include Securinine, okinonellin B, (+)-aspicilin, (−)roccellaric acid and (11R,12S)-oxidoarachidonic acid).

Scheme 6 provides an approach to Roccellaric acid (see *Org. Letters*, 2001, 1315–1318) via substituted γ-butyrolactone 34. Thus, mucohalic acid 1 is converted to allyl compound 14 as described herein. 1,4 addition of cyanide to 14 can provide cyano halo lactone 31. DIBAL reduction of the cyano moiety in 31 will give rise to aldehyde 32. Protection of the aldehyde in 32, followed by selective hydrogenation of the ring double bond provides substituted γ-butyrolactone 34.

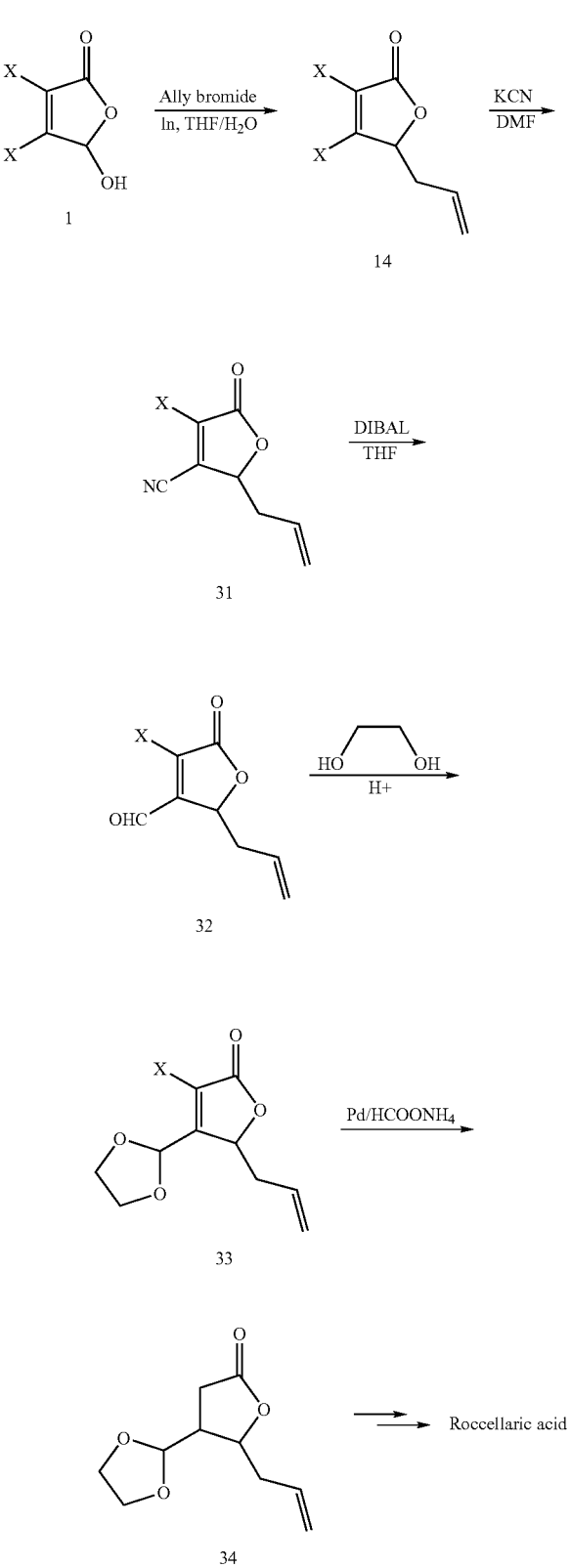

Scheme 6
Synthesis of Key Intermediate 6 in the Synthesis of Roccellaric Acid from Mucohalic Acid.

In another demonstration of the utility of the invention process in preparing biologically active compounds, a dual approach to the antifungal agent incrustosporine 39 is provided in Scheme 7. Thus, mucohalic acid can be readily converted to 14, as provided herein. Aryl coupling to 14 can be achieved via procedures known to the skilled artisan to provide the arylated compound as a mixture of regioisomers 35 and 36. Hydrogenation of the ring double bond in 35 will give rise to the target compound 39. Alternatively, arylation may occur before allylation. Thus, coupling of an aryl group to mucohalic acid can be achieved via procedures known to the skilled artisan to provide the arylated compound as a mixture of regioisomers 37 and 38. Allylation can then be effected according to the procedure disclosed herein to provide allylated compounds 35 and 36, which can be converted to the target compound 39 as provided above.

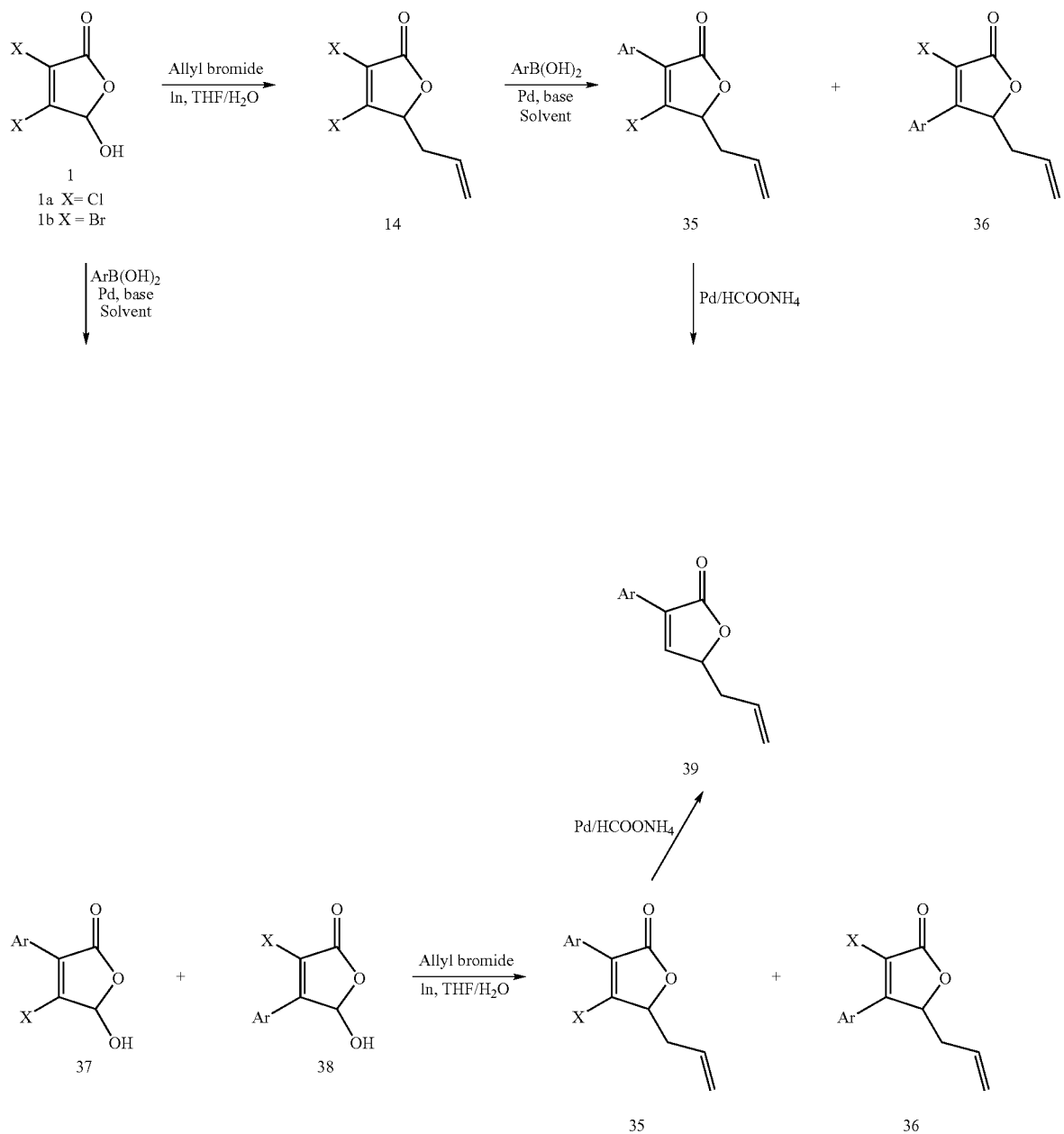

We further exploited mucohalic acid as a building block for other complex molecules, as depicted in Scheme 8. Saturated butyrolactones, such as 4-decanolide A, gamma-dodecanolactone B (a fruit flavor principle, known as or γ-Laurolactone) and whisky lactone C, are widely found in flavors and fragrances. Preparation of saturated γ-butyrolactones was investigated via hydrogenation of 40 or 42, prepared as indicated from mucohalic acid. When 20% Pd/C and Et₃N in THF was used, products 41 and 43 were isolated in excellent yield. Thus, both the Cl and Br atoms are easily removed by hydrogenation of 36 or 37.

Scheme 8
Synthesis of Saturated Butyrolactones

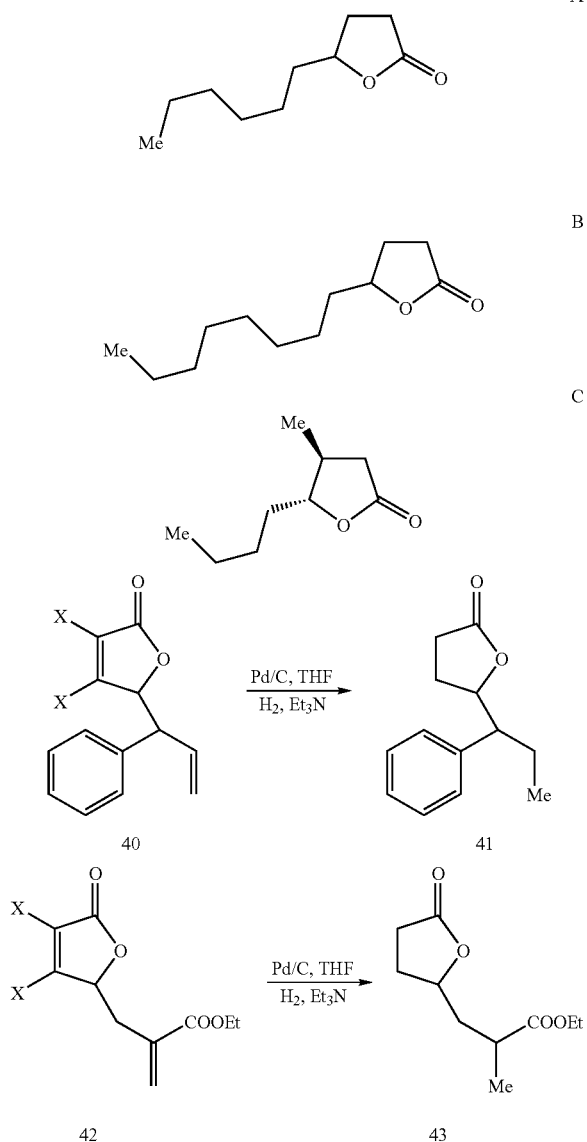

The following examples are intended to illustrate various embodiments of the invention and are not intended to restrict the scope thereof.

EXAMPLE 1

General Procedure A.
Reaction of Mucochloric Acid with Allyl Bromide.

A mixture of mucochloric acid (1.7 g, 10 mmol, 1.0 eq.), allyl bromide (1.5 g, 12 mmol, 1.2 eq.), Indium (1.4 g 12 mmol, 1.2 eq.), and ammonium chloride (53 mg, 1 mmol, 0.1 eq.) in 30 mL (THF/water=1:1) stirred at room temperature for 16 hours. The reaction mixture was then quenched with 1N HCl and extracted with ethyl acetate (3×100 mL). The organic layer was isolated and concentrated at reduced pressure to yield the product 10a as a crude oil. Purification using silica gel chromatography eluting with ethyl acetate/heptane 1:9 provided the allylated product as an oil (1.7 g, 90%) with satisfactory elemental analysis results and correct MS.

EXAMPLE 2

Reaction of Mucobromic Acid with Allyl Bromide. Same as in General Procedure A to provide the allylated product as an oil (1.95 g) in 70% yield with satisfactory elemental analysis results and correct MS.

EXAMPLE 3

Reaction of Mucobromic Acid with Allyl Bromide. Same as in General Procedure A except 1:1 methanol/water was used as the solvent to provide the allylated product as an oil (2.4 g) in 86% yield with satisfactory elemental analysis results and correct MS.

EXAMPLE 4

Reaction of Mucochloric Acid with Cinnamyl Bromide. Same as in General Procedure A to provide the allylated product as a mixture (1.25 g) in 46% yield (See Table 2) with satisfactory elemental analysis results and correct MS.

EXAMPLE 5

Reaction of Mucochloric Acid with Methyl-(2-bromomethyl) Acrylate. Same as in General Procedure A to provide the allylated product as an oil (1.9 g) in 76% yield with satisfactory elemental analysis results and correct MS.

EXAMPLE 6

Reaction of Mucobromic Acid with Methyl-(2-bromomethyl) Acrylate. Same as in General Procedure A to provide the allylated product as an oil (2.5 g) in 74% yield with satisfactory elemental analysis results and correct MS.

EXAMPLE 7

Reaction of Mucobromic Acid with Proparyl Bromide. Same as in General Procedure A to provide the product as a mixture of allenyl and propargylated products (almost 1:1) in 36% yield (See Table 2) with satisfactory elemental analysis results and correct MS.

EXAMPLE 8

General Procedure. Tin Mediated Reaction of Mucohalic Acid with Allyl Bromide.

With Mucochloric Acid. A mixture of mucochloric acid (1.7 g, 10 mmol, 1 eq) with allyl bromide (1.5 g, 1.1 mL, 12 mmol, 1.2 eq.) and tin (1.4 g, 12 mmol, 1.2 eq.), ammonium chloride (53 mg, 1.0 mmol, 0.1 eq.) in 30 mL 1:1 (v/v THF/water) was stirred at 0 degrees C. The mixture was allowed to warm up to room temperature over the course of 24 hours. The reaction was quenched with 1 N aqueous ammonium chloride, then extracted with ethyl acetate at 0 degrees C. The organic extract was concentrated at reduced pressure to yield the crude product which was purified by column chromatography to provide the allylated product. 84% yield.

With Mucobromic Acid. The same procedure was employed as above in the same stochiometry to provide the allylated product. 75% yield.

EXAMPLE 9

Hydrogenation of 3,4-Dichloro-5-(1-phenyl-allyl)-5H-furan-2-one 3,4-Dichloro-5-(1-phenyl-allyl)-5H-furan-2-one (1.1 g, 4.1 mmol, 1.0 eq.), 20% c Pd(OH)$_2$/C (0.2 g), and triethylamine (1.1 g, 10.3 mmol, 2.5 eq.) were combined in 20 mL of tetrahydrofuran. The mixture was hydrogenated at 40 pounds/in$^2$ for 16 hours. The palladium catalyst was removed by filtration and the remaining mixture was concentrated in vacuo to provided the crude product as an oil. The material w2as purified by column chromatography to provide the product as a colorless oil. 83% yield. MS (AP+) 205.1 (M+).

Hydrogenation of 2-[(3,4-Dichloro-5-oxo-2,5-dihydrofuran-2-yl)-phenyl-methyl]-acrylic acid ethyl ester The same procedure as above may be used to provide the hydrogenated carboethoxy product Y.

EXAMPLE 10

Conjugate Addition of Benzyl amine to 5-Allyl-3,4-dibromo-5H-furan-2-one (10b)

A solution of 5-Allyl-3,4-dibromo-5H-furan-2-one (10b) (1.40 g, 5 mmol, 1 rq.) and benzylamine (0.5 g, 1.1 mL, 15 mmol) in NMP (10 mL) was stirred at room temperature for 3 hours. The reaction mixture was quenched with aqueous satured ammonium chloride solution and extracted with ethyl acetate. The ethyl acetate layer was washed with brine, dried, and concentrated to provide the crude conjugate addition adduct 11b. Purification by recrystallization using 4:1 heptane:ethyl acetate to provide 0.8 g (52 percent yield) of the conjugate addition adduct 11b as a solid. MS (AP+) 308.0.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:
1. A process for preparing functionalized butyrolactones of formula

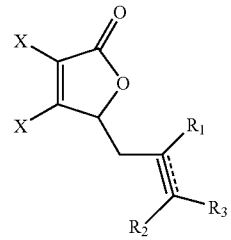

I wherein X is Cl or Br;
R$_1$, R$_2$, and R$_3$ are each independently H, halo, aryl, (C$_1$–C$_6$)alkoxycarbonyl, (C$_1$–C$_6$)alkanoyl, (C$_1$–C$_6$ alkyl), halo(C$_1$–C$_6$ alkyl), heteroaryl(C$_1$–C$_6$)alkyl or aryl (C$_1$–C$_6$ alkyl); and
"- - -" is a bond or is absent, provided that when "- - -" is a bond, R$_1$ and R$_2$ are absent;
comprising:
(a) contacting mucohalic acid 1

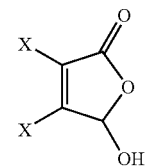

1 wherein X is as defined above;
with halide 2

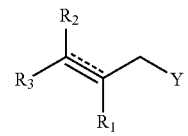

2 wherein Y is Cl, Br, or I;
R$_1$, R$_2$, and R$_3$ are as defined above; and
"- - -" is as defined above;
a metal selected from indium, tin or zinc; and
a catalytic amount of ammonium chloride in a solvent to form the compound of formula I.

2. The process of claim 1, wherein the mucohalic acid 1 is mucochloric acid.

3. The process of claim 1, wherein indium or tin is used.

4. The process of claim 1, wherein "- - -" is absent in halide 2.

5. The process of claim 4, wherein in halide 2, at least one of R$_1$ R$_2$, and R$_3$ is H and the others of R$_1$ R$_2$, and R$_3$ are each independently H, halo, aryl, (C$_1$–C$_6$) alkoxycarbonyl, (C$_1$–C$_6$)alkanoyl, or (C$_1$–C$_6$ alkyl).

6. The process of claim 4, wherein in halide 2, R$_1$ is H, and one of R$_2$ and R$_3$ is H, while the other of R$_2$ and R$_3$ is halo, aryl, (C$_1$–C$_6$)alkoxycarbonyl, (C$_1$–C$_6$)alkanoyl, or (C$_1$–C$_6$ alkyl).

7. The process of claim 4, wherein in halide 2, $R_1$ is aryl, ($C_1$–$C_6$) alkoxycarbonyl, ($C_1$–$C_6$)alkanoyl, or ($C_1$–$C_6$ alkyl), and at least one of $R_2$ and $R_3$ is H.

8. The process of claim 1, wherein in halide 2, "- - -" is a bond, $R_1$ and $R_2$ are absent, and $R_3$ is H, aryl, carboxy ($C_1$–$C_6$)alkyl, ($C_1$–$C_6$)alkanoyl, or ($C_1$–$C_6$ alkyl).

9. The process of claim 1, wherein in step (a), the molar equivalents of mucohalic acid, allylic or propargylic halide, indium, and ammonium chloride are:
 about 1 equivalent of compound of mucohalic acid 1;
 about 1.0 to about 1.5 equivalents of halide 2;
 about 1.0 to about 1.5 equivalents of indium; and
 about 0.1 to about 0.5 equivalents of ammonium chloride.

10. The process of claim 1, wherein in step (a), the molar equivalents of mucohalic acid, allylic or propargylic halide, indium, and ammonium chloride are:
 about 1 equivalent of the compound of mucohalic acid 1;
 about 1.1 to about 1.3 equivalents of halide 2;
 about 1.1 to about 1.3 equivalents of indium; and
 about 0.1 to about 0.3 equivalents of ammonium chloride.

11. The process of claim 1, wherein in step (a), the molar equivalents of mucohalic acid, allylic or propargylic halide, indium, and ammonium chloride are:
 about 1 equivalent of the compound of mucohalic acid 1;
 about 1.2 equivalents of halide 2;
 about 1.2 equivalents of indium; and
 about 0.1 to about 0.2 equivalents of ammonium chloride.

12. The process of claim 1, wherein the solvent is selected from a polar protic or a polar aprotic solvent, in the presence or absence of water.

13. The process of claim 1, wherein the solvent is a polar protic solvent which is an alcohol.

14. The process of claim 1, wherein the solvent is methanol or ethanol, used alone or in combination with water.

15. The process of claim 1, wherein the solvent is a polar aprotic solvent.

16. The process of claim 1, wherein the solvent is tetrahydrofuran, DMPU, used alone or in combination with water.

17. The process of claim 1, wherein the solvent is a room temperature ionic liquid (RTIL).

18. The process of claim 1, wherein the solvent is [bmim][$BF_4$], [bmim][$PF_6$], [bmim][$Tf_2N$], where bmim is 1-butyl-3-methylimidazolium and Tf is $CF_3SO_2$.

19. The process of claim 1, wherein the solvent is approximately a 1:1 mixture of tetrahydrofuran and water.

20. The process of claim 1, wherein the reaction temperature in step (a) is about 0 to about 50° C.

21. The process of claim 1, wherein the reaction temperature in step (a) is about 10 to about 40° C.

22. The process of claim 1, wherein the reaction temperature in step (a) is about 20 to about 30° C.

23. The process of claim 1, wherein the reaction temperature in step (a) is about 22 to about 27° C.

24. The process of claim 1, wherein the reaction pressure of step (a) is about 0.9 to about 1.1 atmospheres.

25. The process of claim 1, wherein the reaction time of step (a) is about 10 to about 60 hours.

26. The process of claim 1, wherein the reaction time of step (a) is about 12 to about 50 hours.

27. The process of claim 1, wherein the reaction time of step (a) is about 14 to about 20 hours.

28. The process of claim 1, wherein the concentration of the mucohalic acid 1 in the solvent in step (a) is about 0.1 Molar to about 1.0 Molar.

29. The process of claim 1, wherein the concentration of mucohalic acid 1 in the solvent in step (a) is about 0.2 Molar to about 0.8 Molar.

30. The process of claim 1, wherein the concentration of mucohalic acid 1 in the solvent in step (a) in the solvent is about 0.3 Molar to about 0.5 Molar.

* * * * *